United States Patent
Fukuma et al.

(10) Patent No.: US 12,226,160 B2
(45) Date of Patent: Feb. 18, 2025

(54) METHOD OF PROCESSING OPTICAL COHERENCE TOMOGRAPHY (OCT) DATA, METHOD OF OCT IMAGING, AND OCT DATA PROCESSING APPARATUS

(71) Applicant: TOPCON CORPORATION, Tokyo (JP)

(72) Inventors: Yasufumi Fukuma, Wako (JP); Hisashi Tsukada, Hachioji (JP); Atsushi Kubota, Itabashi-ku (JP)

(73) Assignee: TOPCON CORPORATION, Tokyo (JP)

( * ) Notice: Subject to any disclaimer, the term of this patent is extended or adjusted under 35 U.S.C. 154(b) by 0 days.

(21) Appl. No.: 18/378,711

(22) Filed: Oct. 11, 2023

(65) Prior Publication Data

US 2024/0041316 A1 Feb. 8, 2024

Related U.S. Application Data

(63) Continuation of application No. 16/917,925, filed on Jul. 1, 2020, now Pat. No. 11,849,996.

(30) Foreign Application Priority Data

Jul. 2, 2019 (JP) ................................. 2019-123431
Jul. 2, 2019 (JP) ................................. 2019-123437
Jul. 11, 2019 (JP) ................................. 2019-129315

(51) Int. Cl.
*G06K 9/00* (2022.01)
*A61B 3/00* (2006.01)
(Continued)

(52) U.S. Cl.
CPC ............ *A61B 3/102* (2013.01); *A61B 3/0025* (2013.01); *A61B 3/12* (2013.01); *A61B 5/0066* (2013.01);
(Continued)

(58) Field of Classification Search
None
See application file for complete search history.

(56) References Cited

U.S. PATENT DOCUMENTS 6,044,181 A * 3/2000 Szeliski ................ G06T 3/4038
382/284
6,434,265 B1 * 8/2002 Xiong ................... G06T 15/506
382/284
(Continued)

FOREIGN PATENT DOCUMENTS

JP 2012-115578 A 6/2012
JP 2013-154121 A 8/2013
(Continued)

OTHER PUBLICATIONS

Shum, Heung-Yeung, and Richard Szeliski. "Construction and refinement of panoramic mosaics with global and local alignment." Sixth International Conference on Computer Vision (IEEE Cat. No. 98CH36271). IEEE, 1998. (Year: 1998).*

(Continued)

*Primary Examiner* — Avinash Yentrapati
(74) *Attorney, Agent, or Firm* — XSENSUS LLP

(57) ABSTRACT

An OCT apparatus of an exemplary aspect includes an OCT scanner, image data generating unit, registration unit, and image data composing unit. The OCT scanner is configured to acquire three dimensional data sets by applying an OCT scan to mutually different three dimensional regions of a sample. The image data generating unit is configured to generate a plurality of pieces of image data from the three dimensional data sets. The registration unit is configured to perform a first registration between the plurality of pieces of image data by applying an image correlation calculation to each of overlap regions in the plurality of pieces of image data. The image data composing unit is configured to
(Continued)

compose the plurality of pieces of image data based on a result of the first registration.

7 Claims, 12 Drawing Sheets

(51) Int. Cl.
    *A61B 3/10*           (2006.01)
    *A61B 3/12*           (2006.01)
    *A61B 5/00*           (2006.01)
    *G01B 9/02*           (2022.01)
    *G01B 9/02091*      (2022.01)
    *G06T 3/14*           (2024.01)
    *G06T 3/20*           (2006.01)
    *G06T 3/60*           (2006.01)
    *G06T 7/32*           (2017.01)

(52) U.S. Cl.
    CPC ..... *G01B 9/02083* (2013.01); *G01B 9/02091* (2013.01); *G06T 3/14* (2024.01); *G06T 3/20* (2013.01); *G06T 3/60* (2013.01); *G06T 7/32* (2017.01); *G06T 2200/04* (2013.01); *G06T 2207/10101* (2013.01); *G06T 2207/20212* (2013.01); *G06T 2207/30041* (2013.01)

(56) References Cited

U.S. PATENT DOCUMENTS

| | | | |
|---|---|---|---|
| 7,884,945 B2 | 2/2011 | Srinivasan et al. | |
| 8,405,834 B2 | 3/2013 | Srinivasan et al. | |
| 10,561,311 B2* | 2/2020 | Tokuyama | A61B 3/10 |
| 2006/0119858 A1 | 6/2006 | Knighton et al. | |
| 2007/0070295 A1 | 3/2007 | Tsukada et al. | |
| 2007/0216909 A1 | 9/2007 | Everett et al. | |
| 2010/0208201 A1 | 8/2010 | Knighton et al. | |
| 2011/0134394 A1* | 6/2011 | Srinivasan | A61B 5/0073 |
| | | | 356/479 |
| 2011/0249910 A1* | 10/2011 | Henderson | G06V 10/993 |
| | | | 382/278 |
| 2012/0140172 A1 | 6/2012 | Torii et al. | |
| 2013/0003077 A1 | 1/2013 | Suehira et al. | |
| 2013/0195336 A1* | 8/2013 | Uchida | A61B 3/102 |
| | | | 382/131 |
| 2013/0229622 A1 | 9/2013 | Murase et al. | |
| 2013/0301001 A1* | 11/2013 | Carnevale | A61B 3/102 |
| | | | 345/632 |
| 2014/0211157 A1* | 7/2014 | Nakahara | A61B 3/102 |
| | | | 351/246 |
| 2014/0293289 A1* | 10/2014 | Reisman | G01B 9/02091 |
| | | | 356/479 |
| 2014/0307057 A1* | 10/2014 | Kang | G06T 1/60 |
| | | | 348/47 |
| 2014/0320810 A1* | 10/2014 | Fukuma | A61B 3/0008 |
| | | | 351/206 |
| 2015/0042952 A1 | 2/2015 | Uchida | |
| 2016/0040976 A1* | 2/2016 | Berkeley | A61B 3/102 |
| | | | 356/479 |
| 2016/0066778 A1* | 3/2016 | Imamura | A61B 3/0025 |
| | | | 351/246 |
| 2016/0198940 A1* | 7/2016 | Shibutani | G06V 40/19 |
| | | | 351/206 |
| 2016/0287068 A1 | 10/2016 | Murase et al. | |
| 2017/0004344 A1* | 1/2017 | Nozato | G06V 40/19 |
| 2017/0209037 A1 | 7/2017 | Sumiya | |
| 2018/0003479 A1 | 1/2018 | Tomatsu et al. | |
| 2018/0303334 A1 | 10/2018 | Tokuyama et al. | |
| 2019/0000313 A1* | 1/2019 | Sadda | G06T 7/0012 |
| 2019/0059723 A1 | 2/2019 | Ono | |
| 2019/0069775 A1* | 3/2019 | Kubach | A61B 3/102 |
| 2019/0150729 A1* | 5/2019 | Huang | A61B 3/1241 |
| 2019/0208121 A1* | 7/2019 | Mayle | G06N 20/00 |
| 2019/0208137 A1* | 7/2019 | Mayle | H04N 5/265 |
| 2019/0365223 A1 | 12/2019 | Ono | |
| 2020/0015675 A1 | 1/2020 | Shibutani et al. | |
| 2022/0015629 A1* | 1/2022 | Seibel | A61B 3/12 |

FOREIGN PATENT DOCUMENTS

| | | |
|---|---|---|
| JP | 2013-180125 A | 9/2013 |
| JP | 2014-188373 A | 10/2014 |
| JP | 2017-023869 A | 2/2017 |
| JP | 2017-074325 A | 4/2017 |
| JP | 2017-196522 A | 11/2017 |
| JP | 6230023 B2 | 11/2017 |
| JP | 2018-023818 A | 2/2018 |
| JP | 6276943 B2 | 2/2018 |
| JP | 2018-117693 A | 8/2018 |
| JP | 2019-005254 A | 1/2019 |
| JP | 2019-041841 A | 3/2019 |

OTHER PUBLICATIONS

Javed, Muhammad Younus, and Usman Qayyum. "Face recognition using processed histogram and phase-only correlation (poc)." 2007 International Conference on Emerging Technologies. IEEE, 2007. (Year: 2007).*

Becker, Douglas E., et al. "Image processing algorithms for retinal montage synthesis, mapping, and real-time location determination." IEEE Transactions on Biomedical engineering 45.1 (1998): 105-118. (Year: 1998).*

Partial European search report issued on Nov. 24, 2020, in corresponding European patent Application No. 20182150.1, 13 pages.

Partial European search report issued on Dec. 2, 2020, in corresponding European patent Application No. 20182152.7, 11 pages.

Zhang et al., "Adaptive Optics with Combined Optical Coherence Tomography and Scanning Laser Ophthalmoscopy for in vivo mouse retina imaging", Proc. of SPIE, vol. 10474, Feb. 22, 2018, pp. 1047427-1-1047427-9, total 9 pages, XP060100531.

Extended European search report issued on Nov. 20, 2020, in corresponding European patent Application No. 20182149.3, 9 pages.

Shuliang Jiao et al., "Simultaneous acquisition of sectional and fundus ophthalmic images with spectral-domain optical Coherence tomography", Optics Express, Jan. 24, 2005, pp. 444-452, vol. 13, No. 2, 2005 optical Society of America, US.

Extended European search report issued on Mar. 5, 2021, in corresponding European patent Application No. 20182150.1, 15 pages.

Akihito UJI et al., "Impact of Multiple En Face Image Averaging on Quantitative Assessment from Optical Coherence Tomography Angiography Images", American Academy of Ophthalmology, Ophthalmology, vol. 124, No. 7, Jul. 2017, pp. 944-952.

M. Pohit et al., "Image registration under translation and rotation in two-dimensional planes using Fourier slice theorem", Applied Optics, Optical Society of America, vol. 54, No. 14, May 10, 2015, pp. 4514-4519.

U.S. Office Action issued Jun. 24, 2021 in U.S. Appl. No. 16/916,154, 39 pages.

U.S. Office Action issued Jun. 24, 2021 in U.S. Appl. No. 16/917,922, 36 pages.

Extended European search report issued on Jan. 17, 2022, in corresponding European patent Application No. 21200117.6.

European Office Action issued Sep. 13, 2022 in corresponding European Patent Application No. 20182149.3, 4 pages.

Japanese Office Action issued Jan. 31, 2023 in corresponding Japanese Patent Application No. 2019-129315 (with machine-generated English translation), 7 pages.

Japanese Office Action issued Feb. 2, 2023 in corresponding Japanese Patent Application No. 2019-123431 (with machine-generated English translation), 10 pages.

Japanese Office Action issued Feb. 14, 2023 in corresponding Japanese Patent Application No. 2019-123437 (with machine-generated English translation), 6 pages.

European Office Action issued Jan. 23, 2023 in corresponding European Patent Application No. 20182150.1, 4 pages.

(56) References Cited

OTHER PUBLICATIONS

European Office Action issued Jan. 31, 2023 in corresponding European Patent Application No. 20182152.7, 3 pages.
Office Action issued on Jul. 25, 2023, in corresponding Japanese patent Application No. 2019-123437, 6 pages.
Office Action issued Sep. 12, 2023 in Japanese Patent Application No. 2019-123431, 6 pages.
Communication pursuant to Article 94(3) EPC issued Dec. 11, 2023, in corresponding European Patent Application No. 20 182 150.1, 3 pages.
Communication pursuant to Article 94(3) EPC issued Dec. 11, 2023, in corresponding European Patent Application No. 21 200 117.6, 3 pages.

* cited by examiner

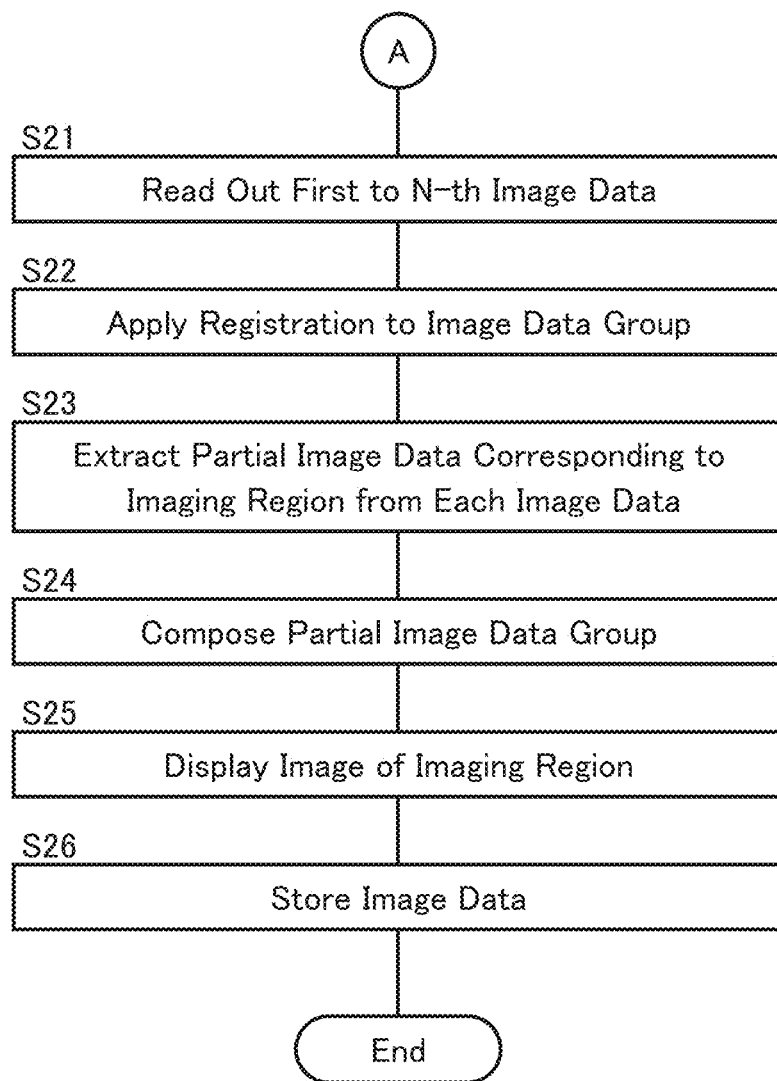

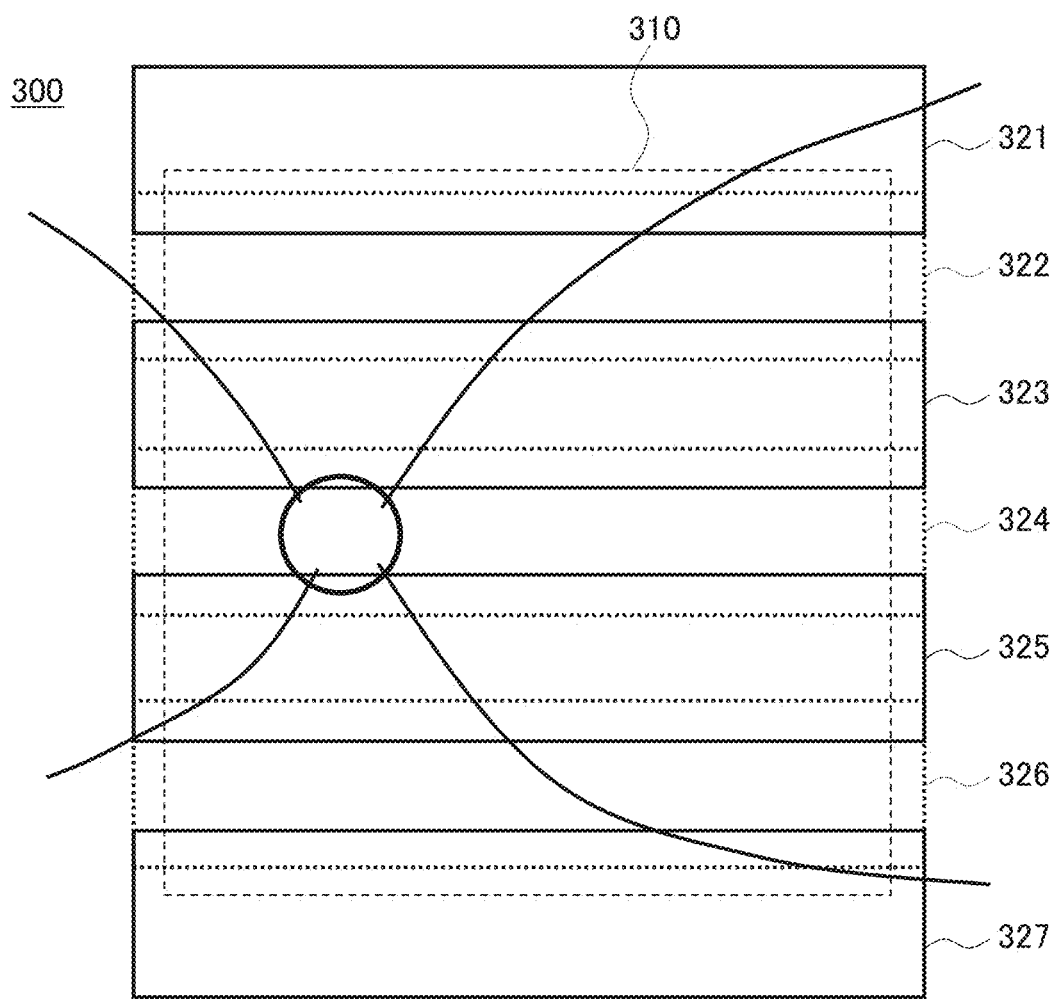

METHOD OF PROCESSING OPTICAL COHERENCE TOMOGRAPHY (OCT) DATA, METHOD OF OCT IMAGING, AND OCT DATA PROCESSING APPARATUS

CROSS-REFERENCE TO RELATED APPLICATIONS

This application is a continuation of U.S. application Ser. No. 16/917,925, filed Jul. 1, 2020, which is based upon and claims the benefit of priority from Japanese Patent Applications No. 2019-123431, filed Jul. 2, 2019, No. 2019-123437, filed Jul. 2, 2019, and No. 2019-129315, filed Jul. 11, 2019; the entire contents of each are incorporated herein by reference.

FIELD

Embodiments described herein relate generally to a method of processing OCT data, a method of OCT imaging, and an OCT data processing apparatus.

BACKGROUND

OCT is an imaging technique capable of representing a light scattering medium at a resolution of micrometer level or less, and is used for medical imaging, nondestructive testing and the like. OCT is a low-coherence-interferometry-based technique and typically utilizes near infrared light to ensure the reaching depth of the light into a sample of a scattering medium.

U.S. Pat. No. 7,884,945 discloses a method of processing an OCT data set represented as a function of optical depths that is obtained by a measurement of backscattering or back reflection in order to acquire OCT data efficiently and to acquire OCT data from a specific region of a sample accurately and in a short time. The method includes a step of analyzing an OCT data set to identify landmark region data of at least the first subset, a step of placing the OCT data set based on the landmark region data, and a step of processing at least the second subset of the OCT data set based on the correspondence between the OCT data set and the landmark region data.

Further, U.S. Pat. No. 8,405,834 discloses a method for monitoring disease progression. The method includes a step of acquiring an OCT survey scan data set represented as a function of optical depths that is obtained by a measurement of backscattering or back reflection, a step of analyzing the survey scan data set to identify a landmark region, a step of assigning a location in the sample or a location relating to a fixed position to an element of the survey scan data set to register part of the survey scan data set representing at least part of a diseased or affected tissue region relating to the landmark region, and a step of monitoring the changes in the diseased or affected tissue region at different points in time.

SUMMARY

An object of the present disclosure is to improve the efficiency of OCT data processing.

Some exemplary aspects relate to a method of processing data acquired by an optical coherence tomography (OCT) scan, the method including: preparing a plurality of three dimensional data sets acquired from a plurality of three dimensional regions of a sample different from each other; generating a plurality of pieces of image data from the plurality of three dimensional data sets; performing a first registration between the plurality of pieces of image data by applying an image correlation calculation to each of a plurality of overlap regions in the plurality of pieces of image data; and composing the plurality of pieces of image data based on a result of the first registration.

Any of the following optional aspects may be combined with an OCT imaging method of some exemplary aspects: for a first image data and a second image data that include mutual overlap regions, the image correlation calculation calculates at least one of a translation amount and a rotation amount between the overlap region in the first image data and the overlap region in the second image data; the image correlation calculation includes a phase only correlation calculation; further including preparing a front image of the sample, and performing a second registration between the plurality of pieces of image data based on the front image prior to the first registration.

Some exemplary aspects relate to a method of imaging using optical coherence tomography (OCT), the method including: acquiring a plurality of three dimensional data sets from a plurality of three dimensional regions of a sample different from each other; generating a plurality of pieces of image data from the plurality of three dimensional data sets; performing a first registration between the plurality of pieces of image data by applying an image correlation calculation to each of a plurality of overlap regions in the plurality of pieces of image data; and composing the plurality of pieces of image data based on a result of the first registration.

Any of the following optional aspects may be combined with an OCT imaging method of some exemplary aspects: further including designating an imaging region in the sample, and setting a plurality of target regions to include the imaging region, wherein the plurality of three dimensional data sets is acquired by sequentially applying an OCT scan to the plurality of target regions; further including acquiring two three dimensional data sets by applying OCT scans to two target regions of the plurality of target regions, generating two pieces of image data from the two three dimensional data sets, evaluating an overlap region of the two pieces of image data, and applying the first registration to at least the two pieces of image data, or applying another OCT scan to at least one of the two target regions, depending on a result of the evaluation; further including changing at least one of the two target regions based on the result of the evaluation, wherein the another OCT scan is applied to a changed target region; further including preparing a front image of the sample, and changing at least one of the two target regions based on the front image, wherein the another OCT scan is applied to a changed target region; further including extracting partial image data corresponding to the imaging region from composite image data obtained by composing the plurality of pieces of image data; further including extracting a partial image data group corresponding to the imaging region from the plurality of pieces of image data based on the result of the first registration, and composing the partial image data group; for a first image data and a second image data that include mutual overlap regions, the image correlation calculation calculates at least one of a translation amount and a rotation amount between the overlap region in the first image data and the overlap region in the second image data; the image correlation calculation includes a phase only correlation calculation.

Some exemplary aspects relate to an optical coherence tomography (OCT) data processing apparatus that processes data acquired by an OCT scan, including: a receiving unit that receives a plurality of three dimensional data sets acquired from a plurality of three dimensional regions of a sample different from each other; an image data generating unit that generates a plurality of pieces of image data from the plurality of three dimensional data sets; a registration unit that performs a first registration between the plurality of pieces of image data by applying an image correlation calculation to each of a plurality of overlap regions in the plurality of pieces of image data; and an image data composing unit that composes the plurality of pieces of image data based on a result of the first registration.

Some exemplary aspects relate to a method of controlling an optical coherence tomography (OCT) data processing apparatus including a processor, the method including: controlling the processor to receive a plurality of three dimensional data sets acquired from a plurality of three dimensional regions of a sample different from each other; controlling the processor to generate a plurality of pieces of image data from the plurality of three dimensional data sets; controlling the processor to perform a first registration between the plurality of pieces of image data by applying an image correlation calculation to each of a plurality of overlap regions in the plurality of pieces of image data; and controlling the processor to compose the plurality of pieces of image data based on a result of the first registration.

Some exemplary aspects relate to an optical coherence tomography (OCT) apparatus including: an OCT scanner that acquires a plurality of three dimensional data sets by applying an OCT scan to a plurality of three dimensional regions of a sample different from each other; an image data generating unit that generates a plurality of pieces of image data from the plurality of three dimensional data sets; a registration unit that performs a first registration between the plurality of pieces of image data by applying an image correlation calculation to each of a plurality of overlap regions in the plurality of pieces of image data; and an image data composing unit that composes the plurality of pieces of image data based on a result of the first registration.

Some exemplary aspects relate to a method of controlling an optical coherence tomography (OCT) apparatus including a processor and an OCT scanner that applies an OCT scan to a sample, the method comprising: controlling the OCT scanner to acquire a plurality of three dimensional data sets from a plurality of three dimensional regions of a sample different from each other; controlling the processor to generate a plurality of pieces of image data from the plurality of three dimensional data sets; controlling the processor to perform a first registration between the plurality of pieces of image data by applying an image correlation calculation to each of a plurality of overlap regions in the plurality of pieces of image data; and controlling the processor to compose the plurality of pieces of image data based on a result of the first registration.

Some exemplary aspects relate to a program that causes a computer to execute the method of any one of the aspects.

Some exemplary aspects relate to a computer-readable non-transitory recording medium storing the program of any one of the aspects.

According to some exemplary aspects, improvements on the efficiency of OCT data processing may be achieved.

BRIEF DESCRIPTION OF THE DRAWINGS

FIG. 3C is a flowchart illustrating the operation of the ophthalmic apparatus (OCT apparatus) according to the exemplary aspect.

FIG. 4B is a schematic diagram for describing the operation of the ophthalmic apparatus (OCT apparatus) according to the exemplary aspect.

DETAILED DESCRIPTION

Figure 1:
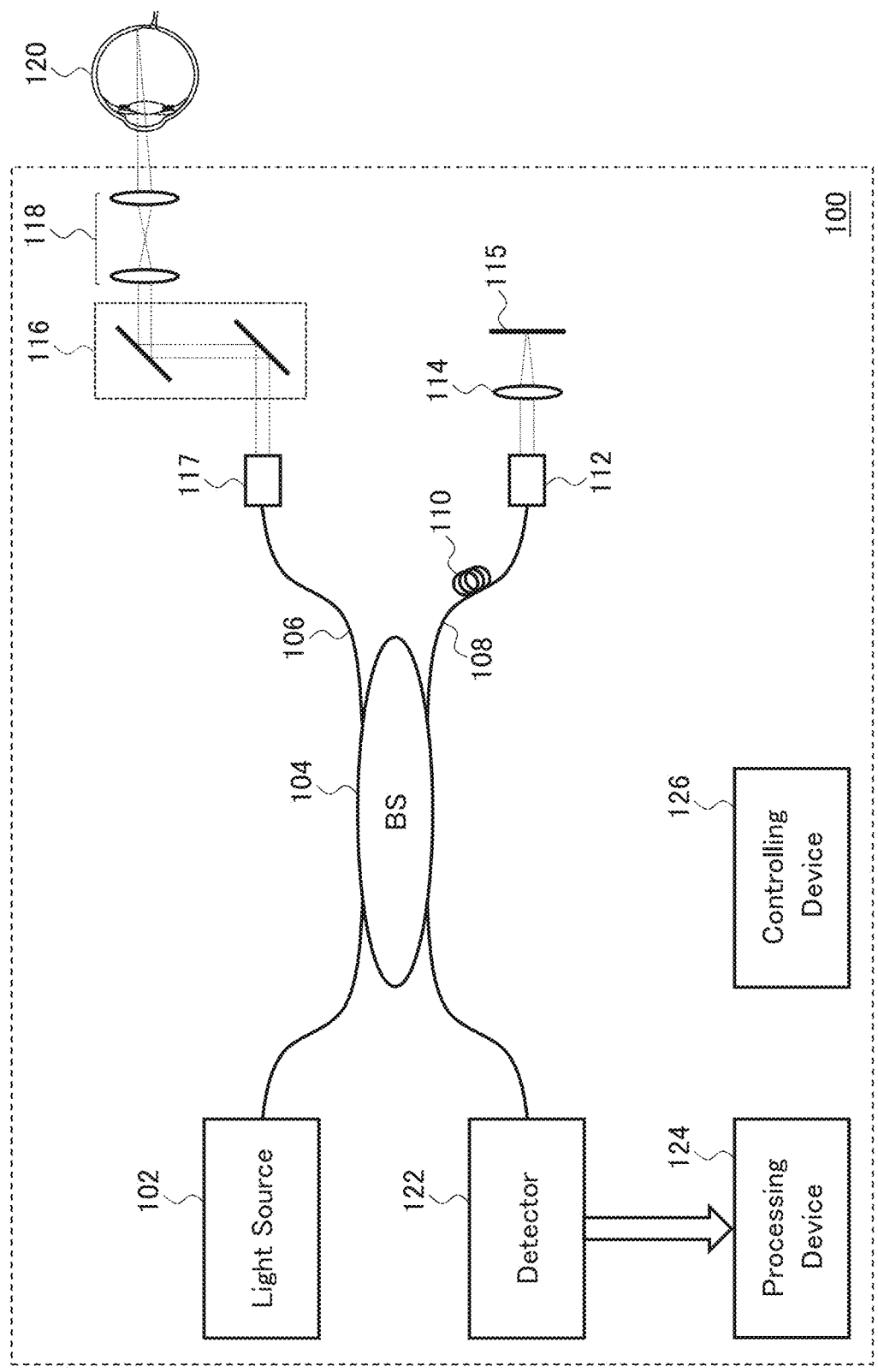
FIG. 1 is a schematic diagram illustrating the configuration of the ophthalmic apparatus (OCT apparatus) according to the exemplary aspect.

Some exemplary aspects of embodiments are described below. Note that any of the items disclosed in the documents cited in the present specification may be incorporated into the exemplary aspects. Also, any items relating to known technologies or known techniques may be incorporated into the exemplary aspects.

Some exemplary aspects relate to techniques for processing a three dimensional data set acquired by applying an OCT scan to a three dimensional region of a sample. These techniques are applicable to various types of processing such as OCT scanning, setting of a region on which an OCT scan is performed, registration between OCT images, analysis, measurement and segmentation of OCT images, thereby contributing to improvements on the efficiency of OCT data processing and/or OCT scanning.

In some exemplary aspects, a "processor" is, for example, a circuit (circuitry) such as a central processing unit (CPU), a graphics processing unit (GPU), an application specific integrated circuit (ASIC), a programmable logic device (e.g., a simple programmable logic device (SPLD)), a complex programmable logic device (CPLD), a field programmable gate array (FPGA), or the like. The processor provides some examples for realizing desired functions, for example, by reading out and executing a program stored in a storage circuit or a storage device.

The type of OCT applicable to some exemplary aspects is optional, and is typically swept source OCT or spectral domain OCT. However, other types of OCT may be employed.

Swept source OCT is an imaging technique performed by splitting light emitted from a wavelength tunable light source into measurement light and reference light, superposing the return light of the measurement light returned from the sample with the reference light to generate interference light, detecting the interference light with a photodetector, and applying Fourier transform and other processes to the detected data acquired according to the wavelength sweeping and the measurement light scanning.

Spectral domain OCT is an imaging technique performed by splitting light emitted from a low coherence light source (broadband light source) into measurement light and reference light, superposing the return light of the measurement light returned from the sample with the reference light to generate interference light, detecting the interference light using a spectrometer to obtain the spectral distribution thereof, and applying Fourier transform and other processes to the spectral distribution detected.

In brief, swept source OCT is an OCT technique of acquiring the spectral distribution of the interference light by time division, and spectral domain OCT is an OCT technique of acquiring the spectral distribution of the interference light by space division.

Types other than such Fourier domain OCT include time domain OCT and en-face OCT (or full field OCT). Time domain OCT introduces mechanical and sequential scanning in the axial direction (Z direction). En-face OCT provides two dimensional imaging of the XY plane orthogonal to the Z direction.

The exemplary aspects described below may be used in ophthalmic imaging, analysis, measurement, evaluation and the like. However, some exemplary aspects may be used in any fields other than ophthalmology such as medical departments other than ophthalmology (e.g., dermatology, dentistry, surgery) and industrial fields (e.g., nondestructive testing).

Figure 2:
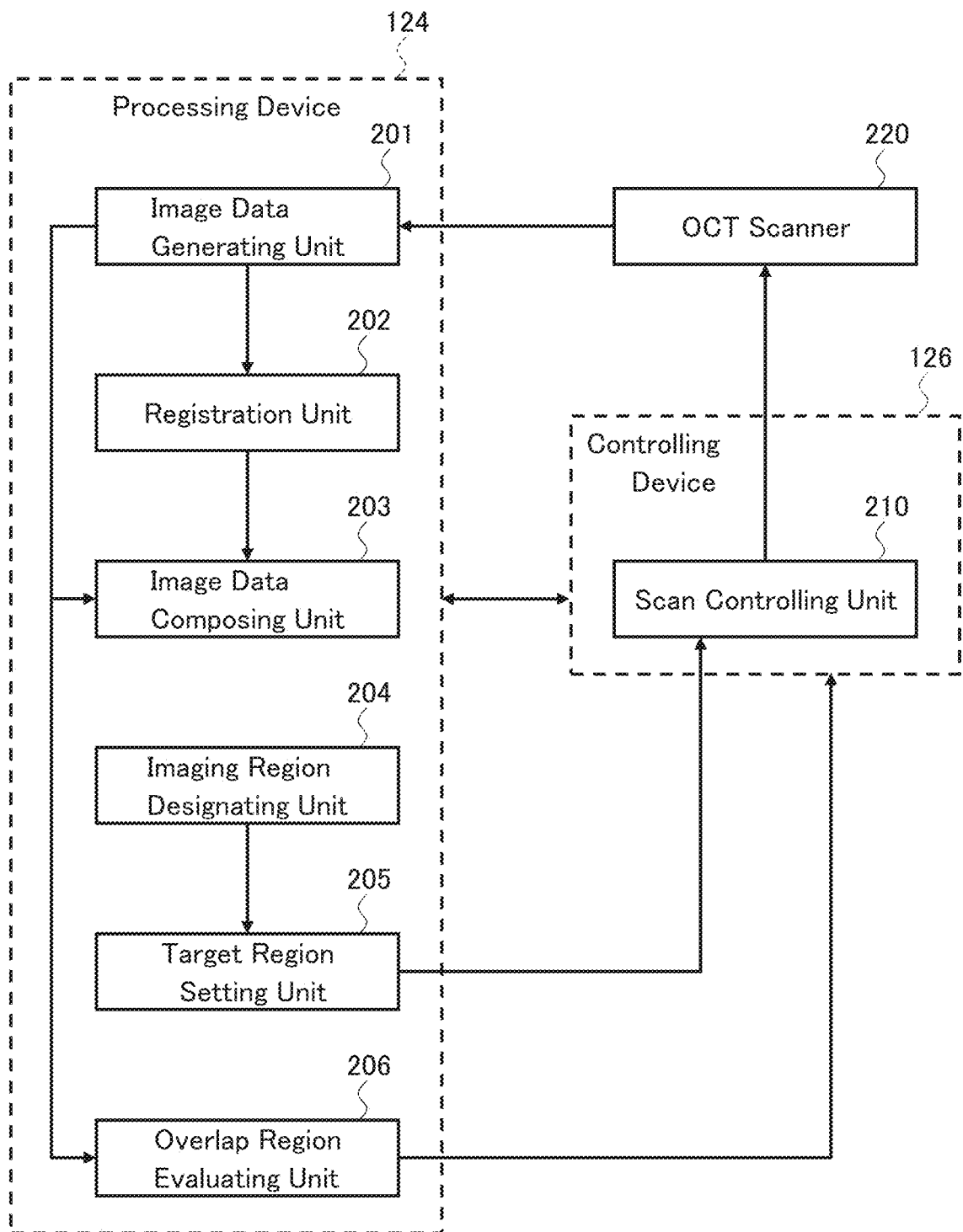
FIG. 2 is a schematic diagram illustrating the configuration of the ophthalmic apparatus (OCT apparatus) according to the exemplary aspect.

FIGS. 1 and 2 show the configuration of the OCT apparatus (ophthalmic apparatus) 100 according to an exemplary aspect. The ophthalmic apparatus 100 provides an OCT imaging method.

To begin with, brief outlines of some features related to the ophthalmic apparatus 100 will be described. The ophthalmic apparatus 100 is configured to acquire three dimensional data sets from mutually different three dimensional regions of a sample (eye). Typically, the three dimensional regions are set in the manner that each of the three dimensional regions partially overlaps one or more other three dimensional regions. The ophthalmic apparatus 100 acquires three dimensional data sets respectively corresponding to the three dimensional regions by sequentially executing OCT scans respectively targeting the three dimensional regions. The order in which the OCT scans are applied, that is, the order assigned to the three dimensional regions is arbitrarily set. For example, an order may be assigned to the three dimensional regions so that the n-th three dimensional region and the (n+1)-th three dimensional region partially and mutually overlap (where n is a positive integer). In another example, in the case where one (or, two or more) three dimensional region partially overlaps with all other three dimensional regions, an order may be arbitrarily assigned to these three dimensional regions. Note that taking eye movements and the like into consideration, it is considerable that a region to which an OCT scan targeting a certain three dimensional region is actually applied does not coincide with this three dimensional region. However, a region that substantially coincides with this three dimensional region may be scanned using fixation and/or tracking. Further, the number of three dimensional data sets acquired from one three dimensional region is not limited to one. For example, by acquiring two or more three dimensional data sets from a single three dimensional region, averaging for image quality improvement and motion contrast data generation (OCT angiography, etc.) may be executed in subsequent processing.

Further, the ophthalmic apparatus 100 is configured to generate a plurality of pieces of image data from three dimensional data sets acquired by the application of the OCT scans to the three dimensional regions. Thereby, a plurality of pieces of image data corresponding to the targeted three dimensional regions is obtained. The above-mentioned averaging and/or motion contrast data generation may be performed at this stage.

In addition, the ophthalmic apparatus 100 is configured to perform registration (the first registration) between the plurality of pieces of image data by applying image correlation calculation to each of the overlap regions of the plurality of pieces of image data corresponding to the targeted three dimensional regions. In other words, the ophthalmic apparatus 100 is configured to arrange (or, register or align) the plurality of pieces of image data according to the image correlations of their overlap regions. Since the three dimensional regions are typically set in the manner that each of them partially overlaps with one or more others as described above, each image data partially overlaps with at least one other image data. By using the image correlation of such overlap regions, registration between these pieces of image data can be performed, and eventually, whole registration between the plurality of pieces of image data can be achieved.

In addition, the ophthalmic apparatus 100 is configured to compose the plurality of pieces of image data based on the result of the whole registration between the plurality of pieces of image data. The resulting image data from such composition is referred to as panoramic image data or montage image data, and is computer graphics image data depicting a wider area than each of the original three dimensional regions.

The ophthalmic apparatus 100 may be configured to designate an imaging region for the sample (eye). For example, the ophthalmic apparatus 100 may designate an imaging region to which an OCT scan is applied, in response to a command or instruction for designating an imaging region from the user. In another example, the ophthalmic apparatus 100 may designate an imaging region based on image data obtained from the sample by itself and/or image data of the sample obtained from another apparatus. In still another example, the ophthalmic apparatus 100 may designate an imaging region with reference to information on an imaging region designated in the past examination of the sample. Such past information is typically stored in a medical data system such as an electronic medical record system. Furthermore, the ophthalmic apparatus 100 may be configured to set target regions to include the imaging region designated. That is, the union of the target regions includes the imaging region designated for the sample. For example, the ophthalmic apparatus 100 may set target regions in response to a command or instruction for setting target regions from the user. In another example, the ophthalmic apparatus 100 may set target regions based on image data obtained from the sample by itself and/or image data of the sample obtained from another apparatus. In still another example, the ophthalmic apparatus 100 may set target regions with reference to information on target regions set in the past examination of the sample. Such past information is typically stored in a medical data system such as an electronic medical record system. In addition, the ophthalmic apparatus 100 acquires three dimensional data sets corresponding to the three dimensional regions by sequentially applying OCT scans to the target regions set to include the imaging region. As described above, a certain target region and a three dimensional region to which an OCT scan is applied correspondingly may not coincide with each other due to the influence of eye movements or the like. However, in some exemplary aspect, a certain target region, a three dimensional region to which an OCT scan is applied correspondingly, and a three dimensional data set acquired by this OCT scan may be associated with each other.

The ophthalmic apparatus 100 acquires two three dimensional data sets by applying OCT scans to two target regions (referred to as a target region pair) of the target regions that have been set to include the imaging region, and then generates two pieces of image data from the two three dimensional data sets. Further, the ophthalmic apparatus 100 may evaluate the overlap region between the two pieces of image data generated. Examples of the evaluation include an evaluation of the size of the overlap region, evaluation of the magnitude of the image correlation value, evaluation of the magnitude etc. of the relative movement amount (e.g., translation amount, rotation amount, etc.) from a preset positional relationship of the two pieces of image data. The ophthalmic apparatus 100 may select a subsequent process according to the result of the evaluation. For example, the ophthalmic apparatus 100 may perform, in a selective manner according to the result of the evaluation, the application of the registration (the first registration described above) to the two pieces of image data, or the application of another OCT scan to at least one target region of the target region pair. In some typical examples, the application of the registration is selected in the event that the evaluation result is good (suitable), and the application of another OCT scan is selected in the event that the evaluation result is not good. The evaluation typically includes a comparison with a preset threshold value. In this case, a good evaluation result is obtained, for example, in the event that the size of the overlap region is equal to or greater than the threshold value, in the event that the image correlation value is equal to or greater than the threshold value, or, in the event that the relative movement amount from the preset positional relationship between the two pieces of image data is less than the threshold value. Such a series of processes (namely, application of OCT scans to a target region pair, generation of an image data pair, evaluation of an overlap region, and execution of selective processing according to the evaluation result) is applied to all of the target regions. For example, target region pairs may be set according to the order assigned to the target regions. Typically, the n-th target region and the (n+1)-th target region may be paired (where n is a positive integer). As a specific example thereof, let "n" also represent the n-th target region, target region pairs (n, n+1) set from five target regions are the following four: (1, 2), (2, 3), (3, 4) and (4, 5). The aspects of the target region pairs are not limited to the type of (n, n+1). For example, a group of target region pairs may be set so that a set of target regions included in all the target region pairs covers the plurality of target regions that have been set to include the imaging region. However, a group of target region pairs may be set so that the set of target regions included in all target region pairs includes only part of the plurality of target regions that have been set to include the imaging region.

In the event that the another OCT scan is applied in response to the result of the overlap region evaluation, a target region pair involved with this newly performed OCT scan may be the same as or at least partially different from the target region pair that has been involved with the previous (or earlier) OCT scan.

As an example of the latter case, the ophthalmic apparatus 100 may be configured to change at least one target region of the target region pairs applied to the previous (or earlier) OCT scan, based on the result of the overlap region evaluation. Typically, the ophthalmic apparatus 100 may use the result of the previous overlap region evaluation in such a way that the next overlap region evaluation gives a good result. For example, the ophthalmic apparatus 100 may change (adjust, correct) one or both of the two target regions of the target region pair so that any of the followings is achieved: the overlap region size becomes equal to or greater than the threshold value; the image correlation value becomes equal to or greater than the threshold value; and the relative movement amount from the preset positional relationship between the two pieces of image data becomes less than the threshold value. The ophthalmic apparatus 100 may be configured to apply another OCT scan to the target region pair reflecting the change. For example, in the event that only one of the target regions of the target region pair is changed, the another OCT scan may be applied only to the changed one.

As another example of changing the target region pair, an ophthalmic apparatus according to another aspect may be configured to prepare a front image of the sample. For example, the ophthalmic apparatus of the present example may have any of the following functions: the function of photographing the sample from the front; the function of photographing the sample from one or more positions other than the front to construct the front image; the function of receiving the front image of the sample from an external device; and the function of reading out the front image of the sample from a recording medium. Further, the ophthalmic apparatus of the present example may be configured to change at least one of the target regions of the target region pair based on the front image acquired. Typically, the change of a target region may include a series of processes as follows: specification (identification) of a partial region of the front image corresponding to that target region; registration between the front image and the image data generated based on a three dimensional data set acquired by an OCT scan on that target region; calculation of a positional difference amount of the image data with respect to the partial region specified; and movement of that target region to compensate for the positional difference amount. The target region change operation is not limited to the movement of the target region, and may include any aspect change in the target region, such as the change in the size, change in the shape, and change in the number of target regions. The ophthalmic apparatus of the present example may be configured to apply another OCT scan to the two target regions after such a change has been made. The ophthalmic apparatus of the present example will be described after the description of the ophthalmic apparatus 100.

In the case where a imaging region is designated for the sample (eye) and target regions are set to include the imaging region, the ophthalmic apparatus 100 may be configured extract partial image data corresponding to the imaging region, from composite image data constructed by composing a plurality of pieces of image data corresponding to the target regions. As a result, three dimensional image data depicting the designated imaging region is obtained. Typically, the extraction of the partial image data includes the registration (alignment, positional adjustment) between the imaging region and the composite image data, and the extraction of the partial image data, from the composite image data, that corresponds to the imaging region identified by the registration. In the event that the above-described front image is acquired, the registration may be performed using the front image.

Instead of extracting the partial image data corresponding to the imaging region after the composition of the plurality of pieces of image data corresponding to target regions, the ophthalmic apparatus 100 may be configured to extract partial image data from each of the plurality of pieces of image data corresponding to the target regions and compose the plurality of pieces of partial image data (the partial image data group) obtained in this way from the plurality of pieces of image data. In other words, in the case where an imaging region is designated for the sample (eye) and target regions are set to include the imaging region, for example, the ophthalmic apparatus 100 may be configured to extract a partial image data group corresponding to the imaging region from the plurality of pieces of imaging data corresponding to the target regions based on the result of the first registration, and then compose the partial image data group. Such a configuration also gives three dimensional image data depicting the imaging region designated.

As described above, the ophthalmic apparatus 100 applies the first registration using the image correlation calculation to two pieces of image data, having their overlap region, out of the plurality of pieces of image data generated based on the three dimensional data sets acquired from the mutually different three dimensional regions of the sample (eye). Any two pieces of image data (any pair of image data) that overlaps in part with one another is referred to as "the first and the second image data". Further, partial image data of the first image data corresponding to that overlap region is referred to as "the overlap region in the first image data"; and, similarly, partial image data of the second image data corresponding to the overlap region is referred to as "the overlap region in the second image data". The image correlation calculation executed by the ophthalmic apparatus 100 may be the calculation of at least one of the translation amount and the rotation amount between the overlap regions in the first and second image data. The translation amount may be a three dimensional translation amount, and typically include three translation amount components in the three directions respectively indicated by the three coordinate axes of a three dimensional orthogonal coordinate system. Likewise, the rotation amount may be a three dimensional rotation amount, and typically include three rotation amount components about the three coordinate axes of the three dimensional orthogonal coordinate system. An example of calculation techniques adoptable for such image correlation calculation is phase only correlation (POC). The phase only correlation may be, for example, the two dimensional technique disclosed in Japanese Patent No. 6,276,943 (International Patent Publication No. WO2015/029675), or a three dimensional technique on the basis of this two dimensional technique. In the case of employing the two dimensional technique, for example, the ophthalmic apparatus 100 may be configured to use the two dimensional technique for each of the XY coordinate system, the YZ coordinate system, and the ZX coordinate system of the three dimensional orthogonal coordinate system (XYZ coordinate system). In the case of adopting the three dimensional technique, for example, the ophthalmic apparatus 100 may be configured to use an arithmetic expression obtained by natural extension of the arithmetic expression of the two dimensional technique to the three dimensional space. As a specific example thereof, arithmetic expressions for the three dimensional phase only correlation may be obtained as natural extensions of the arithmetic expressions (1) to (7) for the two dimensional phase only correlation described in Japanese Patent No. 6,276,943 (International Patent Publication No. WO2015/029675).

The ophthalmic apparatus 100 having at least some of the above-exemplified features will be described below. The exemplary ophthalmic apparatus 100 shown in FIG. 1 includes the light source 102 that generates a light beam. The light source 102 is, for example, a broadband light source or a wavelength tunable light source. The beam splitter (BS) 104 splits the light beam emitted from the light source 102 into a sample light beam (measurement light) and a reference light beam (reference light). In other words, the beam splitter 104 directs part of the light beam emitted from the light source 102 to the sample arm 106 and another part to the reference arm 108.

The reference arm 108 includes the polarization controller 110 and the collimator 112. The polarization controller 110 is used for regulating the reference light beam, for example, for maximizing the interference efficiency. The collimator 112 outputs the reference light beam as a collimated light beam (parallel light beam). The reference light beam output from the collimator 112 is converted into a convergent light beam by the lens 114 and projected onto the reflecting mirror 115. The reference light beam reflected by the reflecting mirror 115 returns to the beam splitter 104 through the reference arm 108. The lens 114 and the reflecting mirror 115 are movable together, whereby the distance from the collimator 112 is changed (in other words, the path length of the reference light beam is changed).

The sample arm 106 guides the sample light beam via the collimator 117, the two dimensional scanner 116, and one or more objective lenses 118, and projects the sample light beam onto the eye 120 as a sample. The two dimensional scanner 116 is, for example, a galvano mirror scanner or a micro electro mechanical systems (MEMS) scanner. The return light of the sample light beam projected on the eye 120 returns to the beam splitter 104 through the sample arm 106. The two dimensional scanner 116 enables OCT scanning on a three dimensional region of the eye 120.

The beam splitter 104 generates an interference light beam by superposing the return light of the reference light beam and the return light of the sample light beam with one another. The interference light beam is guided to the detector 122 and detected by it. With this, the echo time delay of the light is measured from the interference spectrum.

The detector 122 generates a plurality of output sets, based on the composition (superposition) of the return light of the sample light beam supplied from the sample arm 106 and the return light of the reference light beam supplied from the reference arm 108. The result of the composition is interferogram data. For example, the output sets generated by the detector 122 may respectively correspond to light intensities received at different wavelengths output from the light source 102. When the sample light beam is projected sequentially to XY positions by the two dimensional scanner 116, the light intensities detected include information, for the XY positions, on reflection intensity distributions (backscattering intensity distributions) from the inside region of the eye 120 along the depth direction (Z direction).

A three dimensional data set is obtained in the above-described manner. The three dimensional data set includes a plurality of pieces of A-scan data respectively corresponding to the XY positions. Each piece of A-scan data represents a spectral intensity distribution at a corresponding XY position. The three dimensional data set acquired by the detector 122 is sent to the processing device 124.

The processing device 124 executes various kinds of data processing (information processing). The processing device 124 is configured, for example, to execute the following processes: a process of generating a plurality of pieces of image data from three dimensional data sets of the sample; a process of applying the image correlation calculation to each of the overlap regions in the plurality of pieces of image data generated, to perform registration (the first registration described above) between the plurality of pieces of image data; and a process of composing the plurality of pieces of image data based on the result of the first registration. In addition, the processing device 124 is configured to execute processing for realizing at least one of the exemplary features described above. The processing device 124 includes a processor that operates according to a processing program. Some specific examples of the processing device 124 will be described later.

The controlling device 126 executes control of each part of the ophthalmic apparatus 100. For example, the controlling device 126 is configured to perform control to prepare three dimensional data sets acquired from mutually different three dimensional regions of the sample. The control for preparing the three dimensional data set may include, for example, control for applying an OCT scan to the eye 120, and/or control for obtaining a three dimensional data set acquired from the eye 120 from another device or a recording medium. Further, the controlling device 126 is configured to perform control for realizing at least one of the exemplary features described above. The controlling device 126 includes a processor that operates according to a control program. Some specific examples of the controlling device 126 will be described later.

Although not shown in the drawings, the ophthalmic apparatus 100 may further include a display device, an operation device, a communication device, and other elements.

Further description of the processing device 124 and the controlling device 126 will be given with referring to FIG. 2. The processing device 124 includes the image data generating unit 201, the registration unit 202, and the image data composing unit 203. Further, the processing device 124 includes the imaging region designating unit 204 and the target region setting unit 205. In addition, the processing device 124 includes the overlap region evaluating unit 206. Furthermore, the controlling device 126 includes the scan controlling unit 210.

The OCT scanner 220 shown in FIG. 2 is configured to apply an OCT scan to the sample (the eye 120). The OCT scanner 220 of the present aspect includes, for example, the group of optical elements shown in FIG. 1, namely, the light source 102, the beam splitter 104, the sample arm 106 (the collimator 117, the two dimensional scanner 116, the objective lens 118, etc.), the reference arm 108 (the collimator 112, the lens 114, the reflecting mirror 115, etc.), and the detector 122. In some aspects, the OCT scanner may have other configurations.

In the present aspect, the OCT scanner 220 applies an OCT scan to each of the mutually different three dimensional regions of the eye 120 under the control of the scan controlling unit 210, thereby acquiring three dimensional data sets corresponding to the three dimensional regions.

The controlling device 126 executes control of each part of the ophthalmic apparatus 100. Control relating to OCT scanning, among various kinds of control, is performed by the scan controlling unit 210. The scan controlling unit 210 of the present aspect is configured to perform control for the OCT scanner 220. For example, the scan controlling unit 210 of the present aspect may be configured to perform at least control for the light source 102, control for the two dimensional scanner 116, and movement control for the lens 114 and the reflecting mirror 115. The scan controlling unit 210 includes a processor that operates according to a scan controlling program.

The processing device 124 executes various kinds of data processing such as calculation, analysis, measurement, and image processing. The image data generating unit 201, the registration unit 202, and the image data composing unit 203 respectively perform the series of three processes described above, namely, the generation of the plurality of pieces of image data based on the three dimensional data sets, the first registration, and the composition of the plurality of pieces of image data.

The image data generating unit 201 generates image data based on data acquired by the OCT scanner 220. For example, the image data generating unit 201 constructs image data of a cross sectional image of the eye 120 based on the output from the OCT scanner 220. The output is referred to as sampling data or interference signal data. Such image data generating processing includes filtering, fast Fourier transform (FFT) etc. as in conventional OCT techniques (e.g., swept source or spectral domain OCT technique). With such processing, reflection intensity profiles are acquired for the A-lines respectively corresponding to the XY positions, and a group of image data for the A-lines is constructed by performing the imaging process on the reflection intensity profiles. Here, an A-line is a scan path of the measurement light beam in the eye 120, and a reflection intensity profile lies along the Z direction. Further, image data for an A-line is referred to as A-scan image data.

Furthermore, the image data generating unit 201 may be configured to construct a plurality of pieces of A-scan image data according to an OCT scanning mode (OCT scanning protocol), and then arrange the plurality of pieces of A-scan image data to construct two dimensional image data or three dimensional image data. Here, the OCT scanning mode is concerned with, for example, the mode of measurement light beam deflection or the mode of A-scan position movement.

In the case where a plurality of pieces of cross sectional image data is obtained by raster scan or another scanning mode, the image data generating unit 201 may construct stack data by embedding the plurality of pieces of cross sectional image data in a single three dimensional coordinate system. In addition, the image data generating unit 201 may construct voxel data (volume data) by applying voxelization to the stack data.

The image data generating unit 201 may be configured to perform rendering on the stack data or volume data. A rendering technique applied thereto is optional. For example, any of volume rendering, multi planar reconstruction (MPR), surface rendering, and other rendering techniques may be applied thereto. Furthermore, the image data generating unit 201 may be configured to construct a planar image from the stack data or volume data. Examples of the planar image include a front image and en-face image. For example, the image data generating unit 201 may be configured to construct a projection image by integrating the stack data or volume data along their A-lines.

As described above, in the present aspect, the OCT scanner 220 acquires three dimensional data sets corresponding to mutually different three dimensional regions of the eye 120. The three dimensional data sets acquired are input to the image data generating unit 201. The image data generating unit 201 generates (three dimensional) image data from each of the three dimensional data sets input.

Thereby, a plurality of pieces of image data respectively corresponding to the mutually different three dimensional regions of the eye 120 is obtained. The image data generating unit 201 may be configured to be capable of executing arbitrary processing related to the image data generation in the exemplary features described above.

The plurality of pieces of image data generated by the image data generating unit 201 is input to the registration unit 202. The registration unit 202 performs registration (the first registration) between the plurality of pieces of image data, by applying an image correlation calculation to each of the overlap regions in the plurality of pieces of image data input.

Japanese Patent No. 6,276,943 (International Patent Publication No. WO2015/029675) provides a technique that can be used for the image correlation calculation performed by the registration unit 202, for example. When this technique is employed, the registration unit 202 may apply phase only correlation to two pieces of image data to determine a positional difference amount (or, positional deviation or displacement) between two overlap regions in the two pieces of image data. The positional difference amount is, for example, a positional difference amount of the positional relationship between actually-obtained two overlap regions with respect to a predetermined positional relationship between the two three dimensional regions corresponding to the two overlap regions (that is, the two three dimensional regions to which OCT scans are applied for acquiring the two pieces of image data). The positional difference amount typically includes any one or both of a translation amount and a rotation amount. Registration is performed to change the relative position of the two pieces of image data so as to compensate for the positional difference amount determined. In other words, the registration between the two pieces of image data is performed to correct the error in the positional relationship between the two overlap regions actually obtained.

In actual processing, the registration unit 202 may first select two pieces of image data considered to be overlapped from the plurality of pieces of image data. For this selection, for example, the arrangement of (or the positional relationship between) the mutually different three dimensional regions of the eye 120 is referred to. Then, the registration unit 202 may apply the phase only correlation to the two respective overlap regions in the two pieces of image data selected.

Typically, such registration is applied at least once for each of the plurality of pieces of image data corresponding to the mutually different three dimensional regions of the eye 120. That is, the registration is applied to all of the plurality of pieces of image data corresponding to the mutually different three dimensional regions of the eye 120. The registration unit 202 may be able to execute any processing related to the first registration in the exemplary features described above.

For details of the phase only correlation technique and the registration technique using the same, Japanese Patent No. 6,276,943 (International Patent Publication No. WO2015/029675) may be referred to. The applicable registration techniques are not limited to the above examples, and any technique or any modification thereof within the scope of the invention described in Japanese Patent No. 6,276,943 (International Patent Publication No. WO2015/029675) may be applied. For registration, any image correlation technique other than the phase only correlation may be used, and further, any image comparison technique other than the image correlation technique may be used.

The result of registration executed by the registration unit 202 is input to the image data composing unit 203 while the plurality of pieces of image data generated by the image data generating unit 201 is input to the image data composing unit 203. The image data composing unit 203 composes the plurality of pieces of image data input from the image data generating unit 201 based on the result of registration input from the registration unit 202.

More specifically, the image data composing unit 203 first determines the positional relationship (relative position) of the plurality of pieces of image data based on the result of registration. For example, for two pieces of image data that are overlapped one another, the image data composing unit 203 arranges the two pieces of image data so that their overlap regions overlap each other in accordance with the result of registration. By applying such image arrangement processing to all combinations of two pieces of image data having mutual overlap regions, all the positional relationships of the plurality of pieces of image data may be determined. This means that all of the plurality of pieces of image data may be represented in a common three dimensional coordinate system, and also that the plurality of pieces of image data may be embedded in the same three dimensional image space. Note that it is not necessary to perform the image arrangement processing for all combinations of two pieces of image data having mutual overlap regions. Rather, it is sufficient to apply the image arrangement processing at least once to each of the plurality of pieces of image data.

Further, the image data composing unit 203 constructs a single image data by applying a known image composition technique to the plurality of pieces of image data to which the image arrangement processing has been applied. The resulting composite image data is also referred to as montage image data, panoramic image data, or the like.

Note that, instead of composing all of the plurality of pieces of image data generated by the image data generating unit 201, any two or more of the plurality of pieces of image data may be composed. In this case, processing such as registration may be applied only to two or more pieces of image data to be composed.

The image data composing unit 203 may be configured to extract part of the composite image data obtained by the composition of a plurality of pieces of image data. For example, the image data composing unit 203 may be configured to extract partial image data corresponding to the imaging region designated by the imaging region designating unit 204 (described later).

Furthermore, the image data composing unit 203 may be configured to extract part of each of the plurality of pieces of image data (or part of each of two or more pieces of image data out of the plurality of pieces of image data) based on the result of registration performed by the registration unit 202, and then compose the plurality of (or two or more) pieces of partial image data extracted. For example, the image data composing unit 203 may be configured to extract partial image data corresponding to the imaging region designated by the imaging region designating unit 204 (described later) from each of the plurality of pieces of image data (or each of two or more pieces of image data out of the plurality of pieces of image data), and then compose the group of partial image data extracted.

The imaging region designating unit 204 is configured to designate an imaging region for the eye 120. The imaging region indicates a region of the eye 120 to which an OCT scan is applied. The region of the eye 120 to which the OCT scan is applied is a three dimensional region. However, the imaging region designated by the imaging region designating unit 204 is typically a two dimensional region defined by the XY coordinates orthogonal to the axial direction (the Z direction, Z coordinate axis). The area (range) in the Z direction is defined as the predetermined imaging area (default area) in the Z direction for the OCT system mounted on the ophthalmic apparatus 100, for example. Note that in the case where the imaging area in the Z direction is variable, the imaging region designating unit 204 may designate, as an imaging area, a three dimensional region that includes a Z directional area in addition to an XY directional area.

The ophthalmic apparatus 100 may be configured so that the user can perform an operation of designating an imaging region using the operation device (and the display device) mentioned above. In this case, the imaging region designating unit 204 may execute designation of an imaging region in response to an imaging region designation command or instruction from the user. For example, the controlling device 126 displays a front image of the eye 120 on the display device, and the user designates a desired region in the front image using the operation device. Then, the imaging region designating unit 204 records the region designated by the user as coordinate information in the front image. The region defined by the coordinate information is treated as an imaging region.

In another example, the imaging region designating unit 204 may designate an imaging region based on image data acquired by imaging the eye 120 with the ophthalmic apparatus 100, and/or based on image data of the eye 120 obtained from another apparatus. In this case, the imaging region designating unit 204 may, for example, detect a feature site in the image data and determine an imaging region with reference to the detected feature site. Here, the feature site of an eye fundus may be the optic nerve head, the macula, a blood vessel, a lesion, etc. The feature site of an anterior eye segment may be the center of the pupil, the center of gravity of the pupil, the center of the iris, the center of gravity of the iris, the corneal apex, the apex of the front surface of the crystalline lens, the apex on the back surface of the crystalline lens, the ciliary body, the Zinn's zonule, a blood vessel, a lesion, etc. In addition, an imaging region is, for example, a region within which a feature site is placed, and also is a region having a predetermined shape and/or a predetermined size. For example, an imaging region may be a square region having a predetermined size defined on the XY plane, including the optic nerve head and the macula. Furthermore, for example, the midpoint of the line segment connecting the center of the optic nerve head and the fovea centralis is placed at the center of the square region.

In yet another example, the imaging region designating unit 204 may designate the current imaging region with reference to information on the imaging region designated in the past for the eye 120. For example, the controlling device 126 accesses a medical data system with the communication device mentioned above, searches the medical data system for past imaging region information of the eye 120, and inputs the searched imaging region information to the imaging region designating unit 204. The imaging region designating unit 204 uses the imaging region information to designate an imaging region applied to the current imaging of the eye 120.

Information indicating the imaging region designated by the imaging region designating unit 204 is input to the target region setting unit 205. The target region setting unit 205 sets target regions so that the target regions include the imaging region designated by the imaging region designating unit 204. The target region setting unit 205 may assign an order to the of target regions. The order assignment (ordering) of the target regions is executed, for example, in the manner described above.

The ophthalmic apparatus 100 may be configured so that the user can designate the target regions using the operation device (and display device) mentioned above. In this case, the target region setting unit 205 may set the target regions upon receiving a target region designation command or instruction from the user. For example, the controlling device 126 may display a front image of the eye 120 on the display device while overlaying the imaging region on the front image. The user may designate desired regions using the operation device. Then, the target region setting unit 205 may record coordinate information in the front image, for each of the regions designated by the user. The regions defined by such coordinate information are treated as target regions.

In another example, the target region setting unit 205 may set target regions based on image data acquired by imaging the eye 120 with the ophthalmic apparatus 100, and/or, image data of the eye 120 obtained from another apparatus. In this case, for example, the target region setting unit 205 may detect a feature site in the image data and set target regions so that the region representing the feature site detected is included in one of the target regions. Thereby, the image of the detected feature site can be depicted in a suitable manner. Note that in the event that a feature site is large, target regions may be set so that the region representing the feature site is divided and depicted in two or more of the target regions. Similarly, in the event that the registration unit 202 refers to an image of the feature site to execute registration, target regions may be set so that the region representing the feature site is divided and depicted in two or more of the target regions. The feature site may be any of the examples mentioned above or other sites. Each target region may be of a predetermined shape and/or a predetermined size.

In yet another example, the target region setting unit 205 may set the current target regions with reference to information on a plurality of target regions set in the past for the eye 120. For example, the controlling device 126 accesses a medical data system with the communication device mentioned above, searches the medical data system for past target region information of the eye 120, and inputs the searched target region information to the target region setting unit 205. The target region setting unit 205 uses the target region information as target regions applied to the current imaging of the eye 120.

Information indicating the plurality of target regions set by the target region setting unit 205 is input to the scan controlling unit 210. The scan controlling unit 210 controls the OCT scanner 220 so that an OCT scan is sequentially applied to the target regions. Under this control, the OCT scanner 220 acquires three dimensional data sets corresponding to the target regions.

For example, the scan controlling unit 210 controls the OCT scanner 220 to sequentially apply an OCT scan to the target regions in accordance with the order assigned by the target region setting unit 205.

In some examples, the scan controlling unit 210 may be configured to perform sequential OCT scans on the target regions in a successive manner. In other words, the scan controlling unit 210 may be configured to execute the sequential OCT scans for the target regions as a series of operations programmed in advance.

Instead of performing sequential OCT scans without combining with other operations in this way, in some other examples, the scan controlling unit 210 may perform sequential OCT scans on target regions in combination with other operations. For example, the ophthalmic apparatus 100 may be configured to perform OCT scans on the target regions one by one while checking every time whether or not each of the OCT scans has been appropriately performed. Some examples thereof are described below.

Some examples consider a time point at which both an OCT scan on an arbitrary target region (referred to as a reference target region) among the target regions and the generation of image data (referred to as reference image data) based on a three dimensional data set acquired from the reference target region by the OCT scan have been completed. Next, the scan controlling unit 210 controls the OCT scanner 220 so as to apply an OCT scan to a target region (referred to as a new target region) to which the order subsequent to the reference target regions is assigned. Further, the image data generating unit 201 generates image data (referred to as new image data) from three dimensional data set acquired from the new target region. The two target regions consisting of the reference target region and the new target region correspond to the target region pair (n, n+1) described above. Furthermore, the two pieces of image data consisting of the reference image data and the new image data correspond to the aforementioned image data pair.

In the present aspect, the reference image data and the new image data are input to the overlap region evaluating unit 206. The overlap region evaluating unit 206 evaluates the overlap regions in the reference image data and the new image data. This evaluates whether or not the overlap between the reference image data and the new image data is appropriate for the composition of the two pieces of image data.

For example, the overlap region evaluating unit 206 may be configured to perform at least one of the evaluations among the following evaluations: an evaluation based on the sizes of the overlap regions in the reference image data and the new image data; an evaluation based on an image correlation value between the overlap regions in the reference image data and the new image data; and an evaluation based on a relative movement amount with respect to a preset positional relationship between the reference image data and the new image data. In some aspects, the image correlation value is calculated by a phase only correlation calculation, and the evaluation thereof is performed based on at least one of the magnitudes of a translation amount and a rotation amount. Alternatively, an evaluation may be performed based on a correlation value indicating the degree of similarity between the overlap regions in the reference image data and the new image data. Further, the preset positional relationship between the reference image data and the new image data corresponds to, for example, the positional relationship between the reference target region and the new target region.

The evaluation result obtained by the overlap region evaluating unit 206 is input to the controlling device 126. The controlling device 126 may select a control content according to the evaluation result input. According to the evaluation result, the controlling device 126 of the present aspect may select and perform: the application of registration (the first registration described above) to the reference target region and the new target region; or the re-application of OCT scanning to at least one of the reference target region and the new target region. The controlling device 126 of the present aspect may be configured to select the first registration in the event that a "good" evaluation result has been obtained, and select the re-application of OCT scanning (the application of another OCT scan) in the event that a "good" evaluation result has not been obtained.

The evaluation carried out by the overlap region evaluating unit 206 may include threshold processing (i.e., comparison with a preset threshold). For example, the overlap region evaluating unit 206 may be configured to calculate the size of the overlap regions in the reference image data and the new image data, compare the size with a threshold value. The overlap region evaluating unit 206 may be configured to give "good" evaluation result in the case where the size is equal to or larger than the threshold value. Examples of the size of the overlap regions include volume (e.g., size defined in the XYZ coordinate system), area (e.g., size defined in any of the XY coordinate system, the YZ coordinate system, the ZX coordinate system, and a two dimensional coordinate system in an arbitrary orientation), length (e.g., size defined by any of the X coordinate, the Y coordinate, the Z coordinate, and a coordinate axis in an arbitrary orientation), surface area, perimeter, diagonal area, and diagonal length. In this way, the overlap region evaluating unit 206 of the present example is configured to determine whether or not the overlap between the reference image data and the new image data has a sufficient size for image data composition.

The overlap region evaluating unit 206 according to another example may be configured to apply an image correlation calculation to the combination of the overlap region in the reference image data and the overlap region in the new image data, compare the image correlation value obtained by the image correlation calculation with a threshold value, and determine as "good" in the case where the image correlation value is equal to or greater than the threshold value. In this way, the overlap region evaluating unit 206 of the present example is configured to determine whether or not the overlap regions in the reference image data and the new image data have sufficient correlation for image data composition.

The overlap region evaluating unit 206 according to still another example may be configured to determine a positional relationship (a relative position) between the reference image data (the overlap region included therein) and the new image data (the overlap region included therein), calculate an error (a relative movement amount) of the relative position with respect to the positional relationship between the reference target region and the new target region, compare the relative movement amount with a threshold value, and determine as "good" in the event that the relative movement amount is less than the threshold value. In this way, the overlap region evaluating unit 206 of the present example is configured to determine whether or not the positional error, which is the difference between: the location of the overlap regions in the actually-obtained reference image data and the actually-obtained new image data; and the relative position between the reference target region and the new target region set for OCT scanning, is sufficiently small for image data composition.

The ophthalmic apparatus 100 is configured to perform a combination of the followings: sequential OCT scanning for target regions; sequential generation of image data; sequential evaluation of overlap regions; and sequential application of the selection of processing according to evaluation results. Some examples of operations realized by the combination will be described below.

Figure 3A:
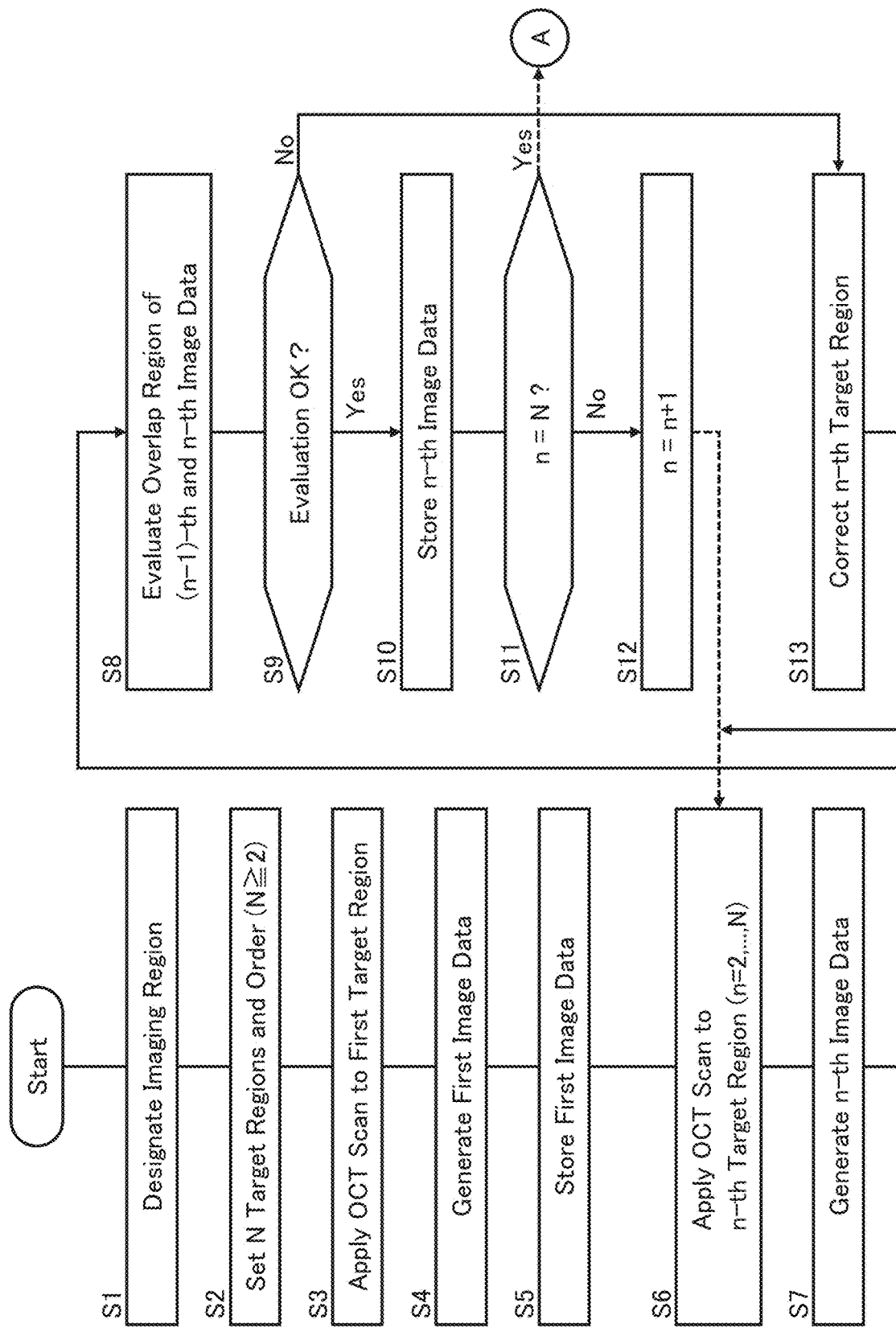
FIG. 3A is a flowchart illustrating the operation of the ophthalmic apparatus (OCT apparatus) according to the exemplary aspect.
Figure 3B:
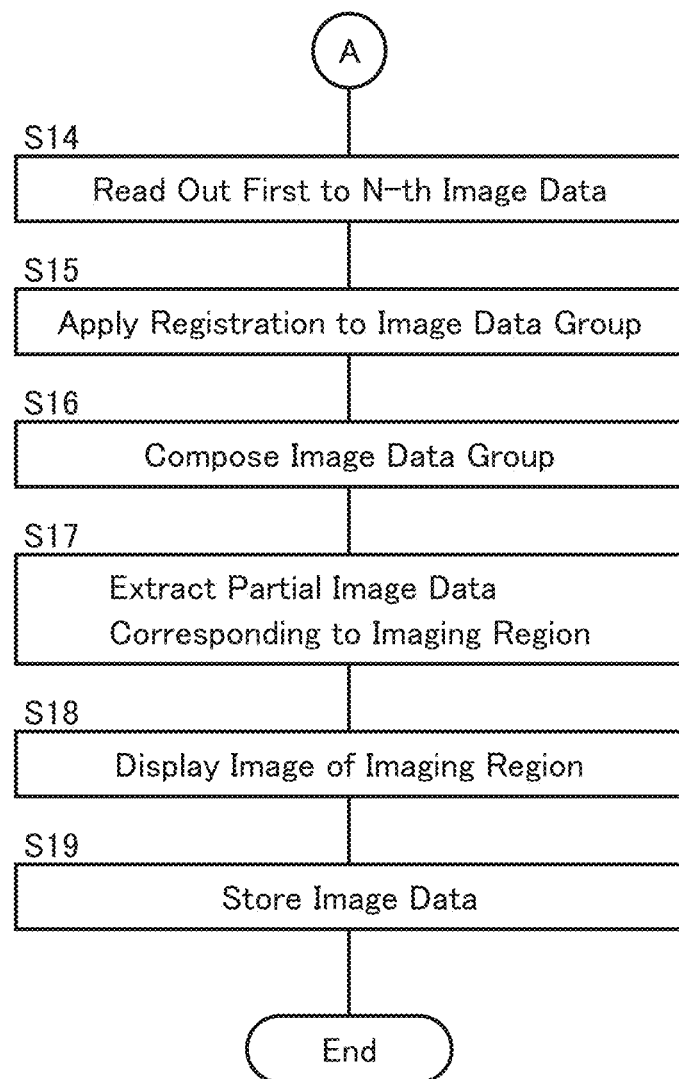
FIG. 3B is a flowchart illustrating the operation of the ophthalmic apparatus (OCT apparatus) according to the exemplary aspect.

Operations of the ophthalmic apparatus 100 will be described. FIGS. 3A, 3B, and 3C show examples of the operations of the ophthalmic apparatus 100. The operations shown in FIGS. 3B and 3C are alternatively applicable. That is, the operation shown in one of FIGS. 3B and 3C may be combined with the operation shown in FIG. 3A. Note that preparatory operations such as alignment, focusing, optical path length adjustment, and polarization adjustment may be performed at arbitrary stages using known methods or techniques.

First, the imaging region designating unit 204 designates an imaging region for the eye 120 (S1).

Figure 4A:
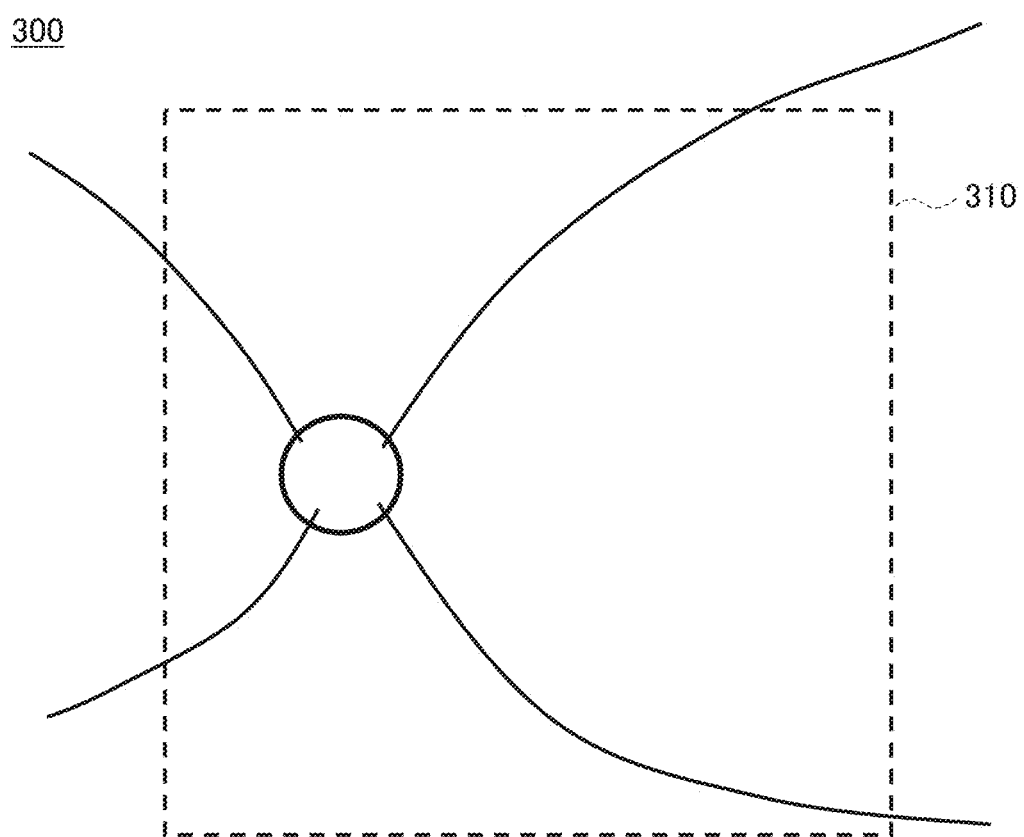
FIG. 4A is a schematic diagram for describing the operation of the ophthalmic apparatus (OCT apparatus) according to the exemplary aspect.

In the example shown in FIG. 4A, the imaging region 310 is designated to include the optic nerve head and the macula of the fundus 300.

Next, the target region setting unit 205 sets target regions to include the imaging region designated in step S1, and sets an order in which OCT scanning is applied to the target regions (S2). In the present example, N number of target regions are set. Here, N is an integer equal to or greater than 2. Further, the target regions are referred to as "the first target region", "the second target region", . . . , "the N-th target region" according to the scan order set in step S2.

In the example shown in FIG. 4B, the seven target regions 321 to 327 are set to include the imaging region 310 illustrated in FIG. 4A. The target regions 321 to 327 are arranged so that any two adjacent target regions partially overlap each other. For example, the two adjacent target regions 322 and 323 are arranged to partially overlap each other, and the two adjacent target regions 323 and 324 are arranged to partially overlap each other. Further, the scan order corresponding to the order of the reference numerals 321 to 327 is assigned to the target regions 321 to 327. In accordance with the scan order, the target region 321 is referred to as "the first target region", the target region 322 is referred to as "the second target region", . . . , and the target region 327 is referred to as "the seventh target region".

After the completion of the target region setting, OCT scanning is started in response to a trigger. First, the scan controlling unit 210 applies an OCT scan to the first target region among the target regions set in step S2 (S3). In the example illustrated in FIG. 4B, an OCT scan is applied to the first target region 321 in this stage.

The image data generating unit 201 generates image data based on a three dimensional data set acquired from the first target region by the OCT scan in step S3 (S4). The image data generated is referred to as "the first image data".

The controlling device 126 stores the first image data generated in step S4 in a storage device (not shown in drawings) (S5). The storage device is typically provided in the ophthalmic apparatus 100 (e.g., provided in the controlling device 126). However, the storage device may be provided outside the ophthalmic apparatus 100.

Next, the scan controlling unit 210 applies an OCT scan to the target region to which the next order has been assigned (S6). After step S5, an OCT scan is applied to the second target region. As shown in FIG. 3A, the present step S6 is repeatedly performed until appropriate image data is obtained from all of the target regions set in step S2. For the following description, it is noted that n=2, . . . , N. Here, N is the number of the target regions set in step S2.

The image data generating unit 201 generates image data based on a three dimensional data set acquired from the n-th target region by the OCT scan in step S6 (S7). This image data is referred to as "the n-th image data".

The controlling device 126 reads out the (n−1)-th image data and the n-th image data from the storage device, and sends them to the overlap region evaluating unit 206. The overlap region evaluating unit 206 executes the evaluation of the overlap regions in the (n−1)-th image data and the n-th image data (S8).

In the event that the result of the evaluation in step S8 is good (S9: Yes), the operation proceeds to step S10. On the other hand, in the event that the result of the evaluation in step S8 is not good (S9: No), the operation proceeds to step S13. In other words, the operation proceeds to step S10 when the n-th image data (overlap region) sufficient for image data composition has been obtained, and the operation proceeds to step S13 when it has not been obtained.

In the event that the result of the evaluation in step S8 is good (S9: Yes), the controlling device 126 stores the n-th image data generated in step S7 in the storage device (S10).

Then, the controlling device 126 determines whether or not n=N (S11). That is, the controlling device 126 determines whether or not appropriate image data has been obtained from every one of the target regions set in step S2. In the event that it is determined to be n=N (S11: Yes), the operation proceeds to step S14 in FIG. 3B (or step S21 in FIG. 3C). On the other hand, in the event that it is determined not to be n=N (S11: No), that is, in the case where n<N, the operation proceeds to step S12.

In the event that it is determined to be n=N in step S11 (S11: No), the controlling device 126 performs control for transferring to the processing related to the next target region (the (n+1)-th target region) (S12). This control includes, for example, control for changing the area to which OCT scanning is applied, such as control of the two-dimensional scanner 116 and/or control for changing the fixation position.

As described above, in the event that the result of the evaluation in step S8 is not good (S9: No), the operation proceeds to step S13. The target region setting unit 205 corrects the n-th target region (S13). For example, the target region setting unit 205 may perform the correction of the n-th target region based on the result of the evaluation in step S8.

Note that, in the case where OCT scanning is sequentially applied to the target regions, it is thought to be desirable to change the n-th target region to which OCT scanning is applied later, among the (n−1)-th target region and the n-th target region as in the present example. However, the (n−1)-th target region may be changed, or both the (n−1)-th target region and the n-th target region may be changed.

The operation returns to step S6 by the control of step S12. Steps S6 to S13 are repeated until it is determined to be n=N in step S11 (S11: Yes). With such repetition, image data appropriate for image data composition is acquired for every one of the target regions set in step S2. In the event that it is determined to be n=N in step S11 (S11: Yes), the operation of the present example proceeds to step S14 in FIG. 3B or to step S21 in FIG. 3C.

Moving now on to FIG. 3B. In the event that the operation proceeds from step S11 to step S14, first, the controlling device 126 reads out the first to N-th image data corresponding to the first to N-th target regions from the storage device (S14). The controlling device 126 sends the N pieces of image data (image data group) read out, to the registration unit 202.

The registration unit 202 applies the registration to the image data group input by the controlling device 126 (S15). Here, each image data included in the image data group has an overlap region, which partly overlaps adjacent image data, appropriate for image data composition. In other words, each image data included in the image data group has an overlap region, which partly overlaps adjacent image data, appropriate for registration.

Figure 4C:
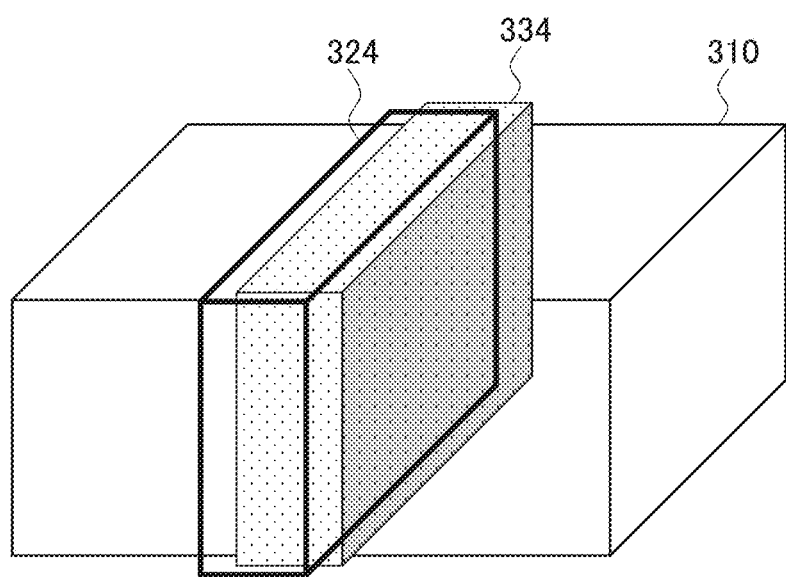
FIG. 4C is a schematic diagram for describing the operation of the ophthalmic apparatus (OCT apparatus) according to the exemplary aspect.

FIG. 4C represents the image data 334 corresponding to the target region 324 shown in FIG. 4B. Even though an OCT scan aims at the target region 324 and is applied to it, the region to which the OCT scan is actually applied is sometimes deviated from the intended target region 324 due to the influence of eye movement or the like.

Figure 4D:
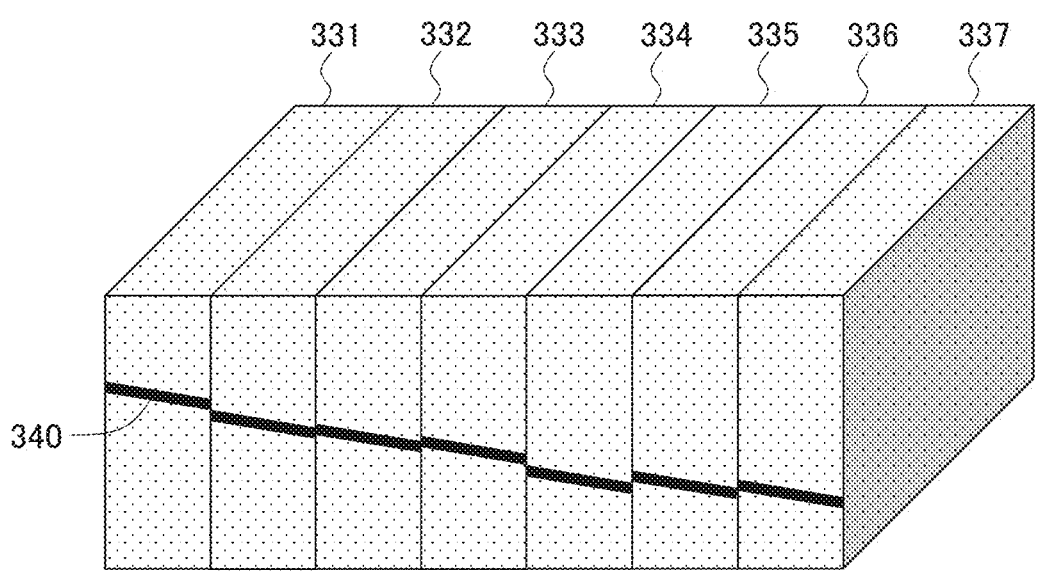
FIG. 4D is a schematic diagram for describing the operation of the ophthalmic apparatus (OCT apparatus) according to the exemplary aspect.

FIG. 4D shows the arrangement of the seven pieces of image data 331 to 337 corresponding to the seven target regions 321 to 327 shown in FIG. 4B according to the arrangement of the seven target regions 321 to 327. If the seven pieces of image data 331 to 337 are arranged in this way, that is, if the seven pieces of image data 331 to 337 are arranged without considering the influence of eye movement or the like, the image 340 of a certain tissue (the tissue image 340) is depicted in a disconnected manner, for example.

By applying the registration in step S15, the influence of eye movement can be compensated for (or, cancelled or eliminated). By applying the registration to the seven pieces of image data 331 to 337 shown in FIG. 4D, the relative positions of the seven pieces of image data 331 to 337 can be adjusted. This leads to the tissue image 340 being depicted in a smoothly connected manner like the actual aspect of that tissue. (See FIG. 4E).

The result of the registration performed in step S15 is input to the image data composing unit 203. The image data composing unit 203 composes the pieces of data in the image data group arranged according to the registration result (S16).

Figure 4E:
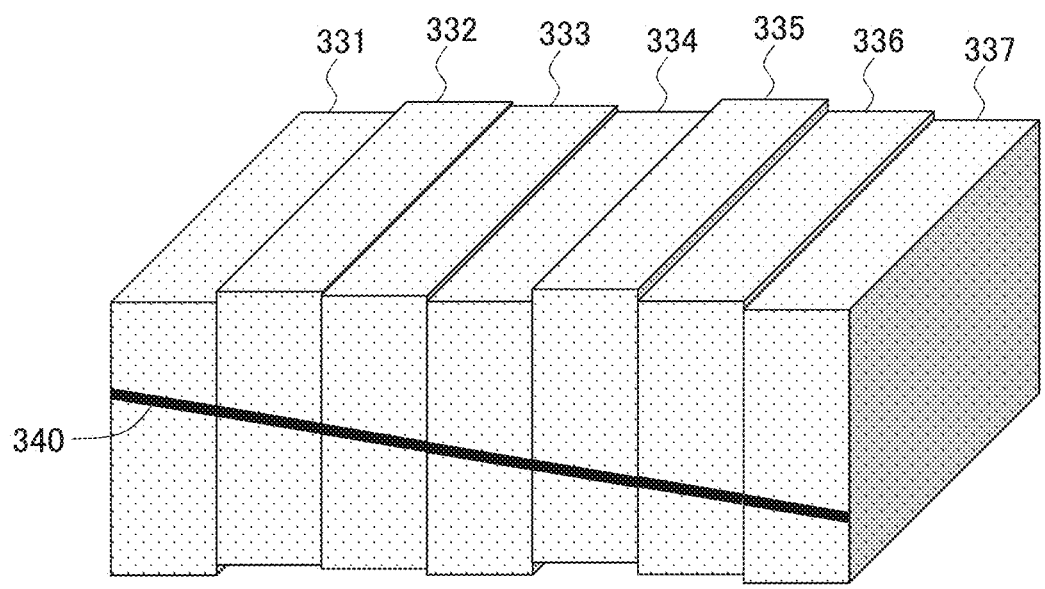
FIG. 4E is a schematic diagram for describing the operation of the ophthalmic apparatus (OCT apparatus) according to the exemplary aspect.

For example, the image data composing unit 203 composes the seven pieces of image data 331 to 337 arranged as shown in FIG. 4E. With this, the composite image data corresponding to the region of the eye 120 including the imaging region designated in step S1 is obtained.

The image data composing unit 203 extracts partial image data corresponding to the imaging region designated in step S1, from the composite image data generated in step S16 (S17).

The controlling device 126 displays the image of the imaging region designated in step S1 on the display device described above, based on the partial image data obtained in step S17 (S18).

The displayed image is obtained by applying rendering to the partial image data that is three dimensional image data. Note that rendering may be performed on the composite image data obtained in step S16, or on any one or more of the first to N-th image data. The user may designate a desired viewpoint or a desired cross section for rendering. Alternatively, a viewpoint or a cross section for rendering may be set in advance.

For example, the controlling device 126 may store any one or more of the following pieces of image data in a storage device not shown in drawings (S19): the partial image data obtained in step S17; the composite image data obtained in step S16; and the first to N-th image data.

The storage device may be, for example, any of an element of the ophthalmic apparatus 100, a peripheral device of the ophthalmic apparatus 100, a device connectable to the ophthalmic apparatus 100 via a communication line, and a portable recording medium. Thus, the operation shown in FIGS. 3A and 3B is completed (End).

Moving now on to FIG. 3C. In the event that the operation proceeds from step S11 to step S21, first, the controlling device 126 reads out the first to N-th image data corresponding to the first to N-th target regions (S21) as in step S14 of FIG. 3B.

Next, the registration unit 202 applies the registration to the image data group input by the controlling device 126 (S22).

The result of the registration executed in step S22 is input to the image data composing unit 203. The image data composing unit 203 extracts partial image data corresponding to the imaging region from each image data included in the image data group (S23). Thereby, a partial image data group corresponding to the image data group is obtained.

Next, the image data composing unit 203 composes the partial image data group extracted from the image data group in step S23, according to the result of the registration (S24). With this, composite image data corresponding to the imaging region designated in step S1 is obtained.

The controlling device 126 applies rendering to the composite image data obtained in step S24 to display the image of the imaging region designated in step S1 on the aforementioned display device (S25).

The controlling device 126, for example, may store any one or more of the following pieces of image data in a storage device not shown in drawings (S26): the composite image data obtained in step S24; the partial image data group obtained in step S23; and the first to N-th image data. Thus, the operation shown in FIGS. 3A and 3C is completed (End).

Figure 5:
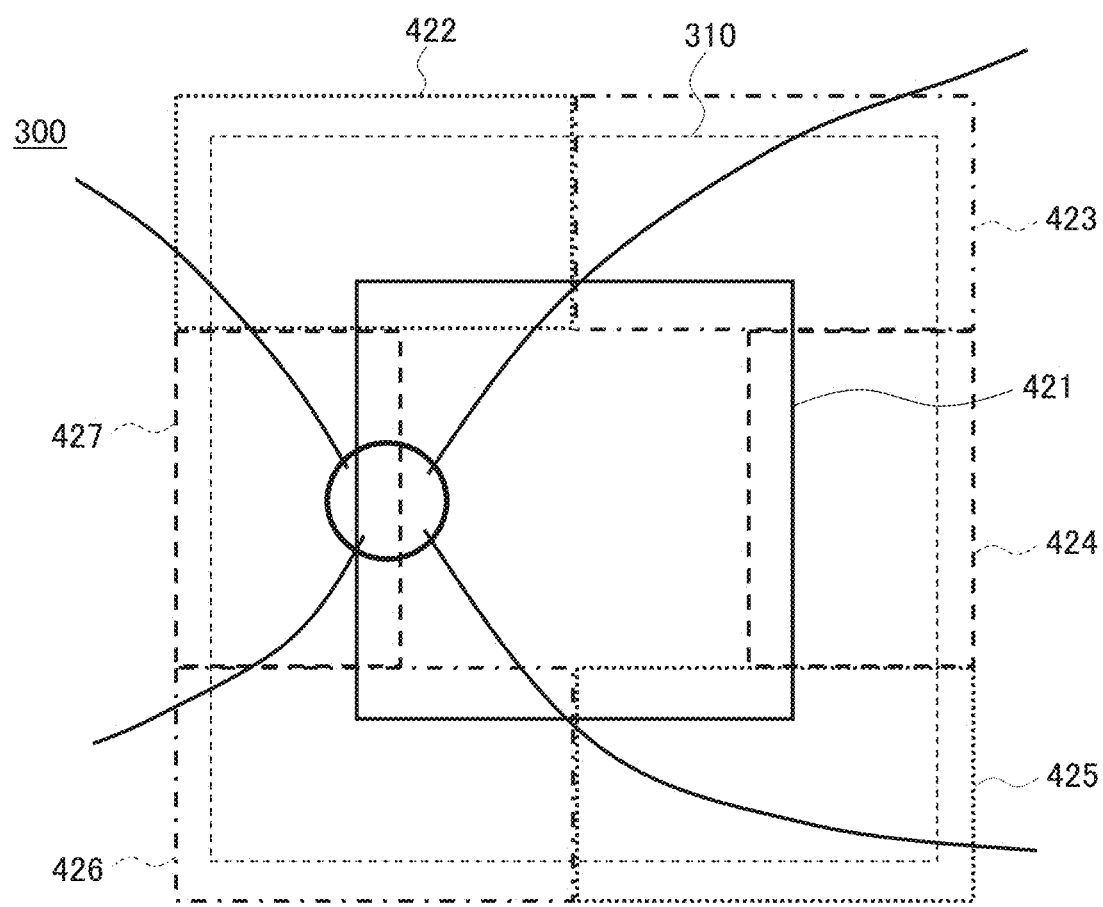
FIG. 5 is a schematic diagram for describing the operation of the ophthalmic apparatus (OCT apparatus) according to the exemplary aspect.

The target regions 321 to 327 shown in FIG. 4B are arranged in a line. However, arrangement aspects of target regions are not limited to this example. For example, as shown in FIG. 5, the target region 421 may be set at the center of the imaging region 310, and the six target regions 422 to 427 may be set around the target region 421. Each of the surrounding (or peripheral) target regions 422 to 427 partially overlaps the central target region 421. Further, any two target regions adjacent to each other among the surrounding target regions 422 to 427 do not overlap each other. In the case where such an arrangement is employed, the registration is applied to the combination of each of the surrounding target regions 422 to 427 and the central target region 421.

Figure 6:
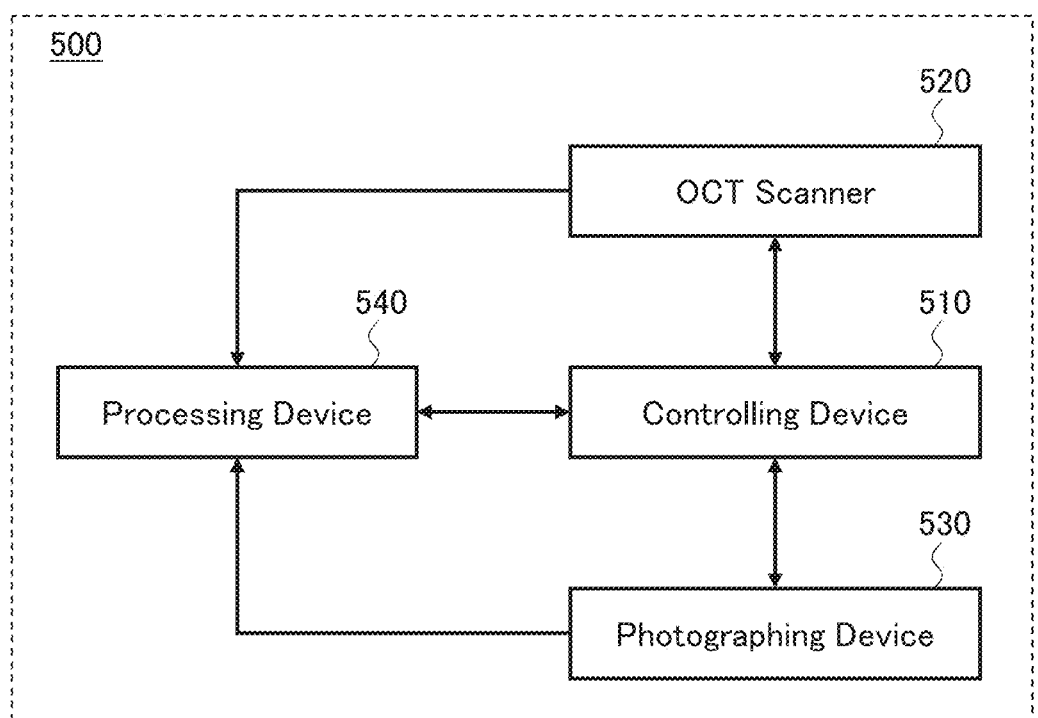
FIG. 6 is a schematic diagram illustrating the configuration of the ophthalmic apparatus (OCT apparatus) according to the exemplary aspect.

The ophthalmic apparatus according to another aspect will be described. The ophthalmic apparatus 500 illustrated in FIG. 6 includes the controlling device 510, the OCT scanner 520, the photographing device 530, and the processing device 540. The controlling device 510 may be configured in the same manner as the controlling device 126 of the ophthalmic apparatus 100. The OCT scanner 520 may be configured in the same manner as the OCT scanner 220 of the ophthalmic apparatus 100. The processing device 540 may be configured in the same manner as the processing device 124 of the ophthalmic apparatus 100. In brief, the ophthalmic apparatus 500 may be obtained by adding the photographing device 530 to the ophthalmic apparatus 100. The sample of the present aspect is an eye. Hereinafter, description will be made with reference to the elements of the ophthalmic apparatus 100 (see FIG. 2, etc.).

The photographing device 530 acquires a front image by photographing the eye. The photographing device 530 may include a camera for photographing the eye (the fundus, the anterior eye segment, etc.) that is located (directly) in front of the eye. Alternatively, the photographing device 530 may include a camera that photographs the eye from one or more positions other than the front position, and a processor that converts the image(s) acquired by the camera into a front image. Instead of the photographing device 530, the ophthalmic apparatus 500 may include a communication device that receives a front image of the eye from an external device, or a reader that reads out a front image of the eye from a recording medium. Typically, the photographing device 530 may be a known ophthalmic modality device such as a fundus camera, a slit lamp microscope, or a surgical microscope.

The ophthalmic apparatus 500 (the target region setting unit 205 in the processing device 540) may execute correction of the target regions based on the front image acquired by the photographing device 530 (see step S13 in FIG. 3A for comparison).

For this purpose, for example, the processing device 540 of the present aspect may be configured to identify a partial region of the front image corresponding to a concerned target region, perform registration between the front image and image data generated based on the three dimensional data set acquired from that target region by the OCT scan, and calculate the positional difference amount of the image data with respect to the partial region.

The controlling device 510 performs control for changing the concerned target region to compensate for the positional difference amount calculated by the processing device 540. The change of the target region may be, for example, any one of the followings: movement of that target region; change in the size of that target region; change in the shape of that target region; and change of the number of the target regions. The controlling device 510 (the scan controlling unit 210) applies another OCT scan to the target region subjected to such a change.

In the ophthalmology field (in particular, diagnosis of eye fundus), infrared illumination is widely used to observe eye fundus by a motion picture without inducing miosis. The purposes of the use of an image obtained by infrared observation (infrared front image) is not limited to the target region correction. For example, an infrared front image may be utilized for designating an imaging region, setting target regions, setting a scan order, evaluating overlap regions, registration (the first registration), composition of image data, and the like. The ophthalmic apparatus 500 may be configured to display or analyze an infrared front image for any of these purposes.

Prior to the first registration, "rough (coarse)" registration (the second registration) may be performed with reference to the infrared front image. The second registration may be performed by comparing each of the plurality of pieces of image data corresponding to the target regions with the infrared front image, and identifying partial regions of the infrared front image respectively corresponding to the plurality of pieces of image data.

Here, the image data corresponding to each target region is three dimensional image data (typically image data defined in the XYZ coordinate system), and the infrared front image is two dimensional image data (typically image data defined in the XY coordinate system). The second registration may include, for example, a process of converting three dimensional image data corresponding to a target region into two dimensional image data defined in the two dimensional coordinate system in which the infrared front image is defined. The two dimensional image data obtained by the conversion of the three dimensional image data may be, for example, the projection image mentioned above.

When the projection (rendering) is applied, the registration between the infrared front image and the three dimensional image data may be performed using the result of the registration between the infrared front image and the projection image.

According to the second registration as described above, rough image registration in the XY directions may be carried out. In the first registration performed after the second registration, registration in the Z direction may be performed in addition to precise (fine) registration in the XY directions. Registrations in rotational directions may be performed in the same manner as the registrations in the coordinate axis directions.

Some effects of the ophthalmic apparatuses (OCT apparatuses) 100 and 500 of the exemplary aspects will be described.

The ophthalmic apparatus 100 (500) includes the OCT scanner 220 (520), the image data generating unit 201, the registration unit 202, and the image data composing unit 203. The OCT scanner 220 acquires three dimensional data sets from mutually different three dimensional regions of the eye 120. The image data generating unit 201 generates a plurality of pieces of image data from the three dimensional data sets acquired by the OCT scanner 220. The registration unit 202 performs the first registration between the plurality of pieces of image data generated by the image data generating unit 201, by applying image correlation calculation to each of the overlap regions in the plurality of pieces of image data. The image data composing unit 203 composes the plurality of pieces of image data corresponding to the mutually different three dimensional regions based on a result of the first registration performed by the registration unit 202.

According to the ophthalmic apparatus 100 thus configured, image data composition can be performed after the registration using the image correlation calculation between three dimensional image data. Therefore, composite image data corresponding to a wide region of the sample can be acquired without having to perform processing relating to landmarks as in the inventions described in U.S. Pat. Nos. 7,884,945 and 8,405,834. This makes it possible to improve effective utilization of resources required for processing and shorten processing time, thereby achieving further efficiency improvement in OCT data processing. Consequently, real-time processing can be preferably performed, for example.

The ophthalmic apparatus 100 (500) may further include the imaging region designating unit 204 and the target region setting unit 205. The imaging region designating unit 204 designates an imaging region for the sample. The target region setting unit 205 sets target regions to include the imaging region designated by the imaging region designating unit 204. Then, the OCT scanner 220 (520) is capable of sequentially applying OCT scanning to the target regions set by the target region setting unit 205, thereby acquiring three dimensional data sets corresponding to the target regions (that is, corresponding to the mutually different three dimensional regions).

According to such a configuration, composite image data can be preferably acquired for a desired imaging region.

The ophthalmic apparatus 100 (500) may further include the overlap region evaluating unit 206. If this is the case, the OCT scanner 220 (520) may acquire two pieces of three dimensional data sets by applying OCT scans to two target regions among the target regions set by the target region setting unit 205. The image data generating unit 201 can generate two pieces of image data from the two pieces of three dimensional data sets acquired from the two target regions. The overlap region evaluating unit 206 evaluates the overlap regions in the two pieces of image data corresponding to the two target regions generated by the image data generating unit 201. Then, the ophthalmic apparatus 100 (500) performs the application of the first registration to at least the two pieces of image data, or the application of another OCT scan (the re-application of an OCT scan) to at least one of the two target regions, according to the result of the evaluation executed by the overlap region evaluating unit 206.

According to such a configuration, the first registration or the re-application of the OCT scan may be performed in a selective manner together with the evaluation of the overlap regions. Typically, the first registration is selected in the event that the overlap regions between image data is preferable, and the re-application of the OCT scan is selected in the event that the overlap regions between image data is not preferable. Thereby, the image data may be acquired again in the event that the overlap regions are not appropriate, and the first registration and image data composition may be performed using preferable overlap regions.

In the ophthalmic apparatus 100, the target region setting unit 205 may change at least one of the two target regions based on the result of the evaluation performed by the overlap region evaluating unit 206. The OCT scanner 220 may perform re-application of the OCT scan to the target region(s) that has been changed by the target region setting unit 205.

According to such a configuration, the target region(s) can be adjusted before the re-application of OCT scanning. This increases the possibility of obtaining a preferable overlap region by the OCT scan in the re-application.

The ophthalmic apparatus 500 may further include a device for preparing a front image of the sample (e.g., the photographing device 530, a communication device, a reader, etc.). In this case, the target region setting unit 205 may change at least one of the two target regions based on the front image. The OCT scanner 220 may apply another OCT scan to the target region(s) that has been changed by the target region setting unit 205.

According to such a configuration, the target region can be adjusted before the application of another OCT scan. This increases the possibility of obtaining a preferable overlap region(s) by the another OCT scan.

In the case where the ophthalmic apparatus 500 includes a device for preparing a front image of the sample (e.g., the photographing device 530, a communication device, a reader, etc.), the registration unit 202 may perform the second registration between the plurality of pieces of image data based on the front image before the first registration.

According to such a configuration, the first registration (precise, fine registration) may be performed taking the overlap regions into account after the second registration using the front image for roughly performing relative positional alignment of the plurality of pieces of image data. With this, the quality of registration can be improved.

In the ophthalmic apparatus 100 (500), the image data composing unit 203 may extract partial image data corresponding to the imaging region designated by the imaging region designating unit 204, from the composite image data obtained by composing the plurality of pieces of image data corresponding to the target regions.

With such a configuration, the reliability of acquiring image data of a desired imaging region (i.e., the reliability of acquiring partial image data) can be improved.

In the ophthalmic apparatus 100 (500), the image data composing unit 203 may extract a partial image data group each corresponding to the imaging region designated by the imaging region designating unit 204, from the plurality of pieces of image data respectively corresponding to the target regions, based on the result of the first registration executed by the registration unit 202. In addition, the image data composing unit 203 may generate composite mage data by composing the partial image data group extracted from the plurality of pieces of image data.

With such a configuration, the reliability of acquiring image data of a desired imaging region (i.e., the reliability of acquiring partial image data) can be improved.

In the ophthalmic apparatus 100 (500), the image correlation calculation performed by the registration unit 202 for the first and second image data having overlap regions may calculate at least one of the translation amount and the rotation amount between the overlap regions in the first and second image data. The image correlation calculation may include phase only correlation calculation.

According to such a configuration, the positional relationship between the first and second image data can be obtained in an efficient manner owing to the utilization of image correlation (e.g., phase only correlation), without having to perform processing, like landmark detection, that requires a large amount of resources.

As described above, the sample of the present aspect is a living eye, but an OCT apparatus used for measurement of samples other than living eyes may have the same and/or like functions and configurations. In other words, any of the items (functions, hardware configurations, software configurations, etc.) regarding the ophthalmic apparatus 100 (500) may be combined with an OCT apparatus of any aspect. The items combined yield or provide corresponding actions and effects.

Some aspects relate to a method of controlling an OCT apparatus that includes a processor and an OCT scanner that applies an OCT scan to a sample. The control method may include at least the following steps: a step of controlling the OCT scanner to acquire three dimensional data sets from mutually different three dimensional regions of the sample; a step of controlling the processor to generate a plurality of pieces of image data from the three dimensional data sets; a step of controlling the processor to perform the first registration between the plurality of pieces of image data by applying an image correlation calculation to each of overlap regions in the plurality of pieces of image data; and a step of controlling the processor to compose the plurality of pieces of image data based on a result of the first registration.

According to the control method of an OCT apparatus described above, composite image data corresponding to a wide region of the sample can be acquired without having to perform processing relating to landmarks. This makes it possible to improve effective utilization of resources required for processing and shorten processing time, thereby achieving further efficiency improvement in OCT data processing. Consequently, real-time processing can be preferably performed, for example.

Any of the items (functions, hardware configurations, software configurations, etc.) regarding the ophthalmic apparatus 100 (500) may be combined with the control method of the present aspect. The items combined yield or provide corresponding actions and effects.

Some aspects relate to a program that causes a computer to execute such a control method of an OCT apparatus. Any of the items described regarding the ophthalmic apparatus 100 (500) may be combined with the program. Further, some aspects relate to a computer-readable non-transitory recording medium storing such a program. Any of the items described regarding the ophthalmic apparatus 100 (500) may be combined with the recording medium.

The ophthalmic apparatus 100 (500) functions as an OCT data processing apparatus that processes data acquired by OCT scanning. The ophthalmic apparatus 100 (500) includes the OCT scanner 220 (520) as an element of performing OCT scanning; however, the OCT data processing apparatus may not include such an OCT scanning element. For example, the OCT data processing apparatus includes a receiving unit that includes the communication device and/or the reader described above, and receives three dimensional data sets acquired from mutually different three dimensional regions of a sample from the outside. The image data generating unit 201 generates a plurality of pieces of image data from the three dimensional data sets received from the outside by the receiving unit. The registration unit 202 performs the first registration between the plurality of pieces of image data, by applying an image correlation calculation to each of the overlap regions in the plurality of pieces of image data generated by the image data generating unit 201. The image data composing unit 203 composes the plurality of pieces of image data based on a result of the first registration executed by the registration unit 202.

According to the control method of an OCT data processing apparatus described above, composite image data corresponding to a wide region of the sample can be acquired without having to perform processing relating to landmarks. This makes it possible to improve effective utilization of resources required for processing and shorten processing time, thereby achieving further efficiency improvement in OCT data processing. Consequently, real-time processing can be preferably performed, for example.

Any of the items (functions, hardware configurations, software configurations, etc.) regarding the ophthalmic apparatus 100 may be combined with the control method of the present aspect. The items combined yield or provide corresponding actions and effects.

Some aspects relate to a program that causes a computer to execute such a control method of an OCT data processing apparatus. Any of the items described regarding the ophthalmic apparatus 100 (500) may be combined with the program. Further, some aspects relate to a computer-readable non-transitory recording medium storing such a program. Any of the items described regarding the ophthalmic apparatus 100 (500) may be combined with the recording medium.

Some aspects of an OCT apparatus (e.g., the ophthalmic apparatus 100 or 500), some aspects of a method of controlling an OCT apparatus, some aspects of an OCT data processing apparatus, or some aspects of a method of controlling an OCT data processing apparatus provide an imaging method using OCT.

The OCT imaging method of some aspects may include at least the following steps: a step of acquiring three dimensional data sets from mutually different three dimensional regions of a sample; a step of generating a plurality of pieces of image data from the three dimensional data sets; a step of performing the first registration between the plurality of pieces of image data by applying an image correlation calculation to each of the overlap regions in the plurality of pieces of image data; and composing the plurality of pieces of image data based on a result of the first registration.

Any of the items (functions, hardware configurations, software configurations, etc.) regarding the ophthalmic apparatus 100 (500) may be combined with the OCT imaging method of the present aspect. The items combined yield or provide corresponding actions and effects.

Some aspects relate to a program that causes a computer to execute such an OCT imaging method. Any of the items described regarding the ophthalmic apparatus 100 (500) may be combined with the program. Further, some aspects relate to a computer-readable non-transitory recording medium storing such a program. Any of the items described regarding the ophthalmic apparatus 100 (500) may be combined with the recording medium.

Some aspects of an OCT apparatus (e.g., the ophthalmic apparatus 100 or 500), some aspects of a method of controlling an OCT apparatus, some aspects of an OCT data processing apparatus, or some aspects of a method of controlling an OCT data processing apparatus provide a method of processing OCT data.

The OCT data processing method of some aspects may include at least the following steps: a step of preparing three dimensional data sets acquired from mutually different three dimensional regions of a sample; a step of generating a plurality of pieces of image data from the three dimensional data sets; a step of performing the first registration between the plurality of pieces of image data by applying an image correlation calculation to each of the overlap regions in the plurality of pieces of image data; and a step of composing the plurality of pieces of image data based on a result of the first registration.

Any of the items (functions, hardware configurations, software configurations, etc.) regarding the ophthalmic apparatus 100 (500) may be combined with the OCT data processing method of the present aspect. The items combined yield or provide corresponding actions and effects.

Some aspects relate to a program that causes a computer to execute such an OCT data processing method. Any of the items described regarding the ophthalmic apparatus 100 (500) may be combined with the program. Further, some aspects relate to a computer-readable non-transitory recording medium storing such a program. Any of the items described regarding the ophthalmic apparatus 100 (500) may be combined with the recording medium.

The non-transitory recording medium may be in any form, and examples thereof include a magnetic disk, an optical disk, a magneto-optical disk, a semiconductor memory, and the like.

While certain embodiments have been described, these embodiments have been presented by way of example only, and are not intended to limit the scope of the inventions. Indeed, the novel embodiments described herein may be embodied in a variety of other forms; furthermore, various omissions, substitutions, additions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method of imaging using optical coherence tomography (OCT), the method comprising:
    designating an imaging region in a sample with reference to information on a past imaging region designated in a past examination of the sample;
    setting a plurality of target regions to include the imaging region with reference to information on past target regions designated in the past examination of the sample;
    acquiring a plurality of three dimensional data sets from a plurality of three dimensional regions of a sample different from each other by sequentially applying an OCT scan to the plurality of target regions;
    generating a plurality of pieces of image data from the plurality of three dimensional data sets;
    performing a first registration between the plurality of pieces of image data by applying an image correlation calculation to each of a plurality of overlap regions in the plurality of pieces of image data;

composing the plurality of pieces of image data based on a result of the first registration; and extracting a partial image data group corresponding to the imaging region from the plurality of pieces of image data based on the result of the first registration, and composing the partial image data group.

2. The OCT imaging method of claim 1, wherein for a first image data and a second image data that include mutual overlap regions, the image correlation calculation calculates at least one of a translation amount and a rotation amount between the overlap region in the first image data and the overlap region in the second image data.

3. The OCT imaging method of claim 2, wherein the image correlation calculation includes a phase only correlation calculation.

4. The OCT imaging method of claim 1, further comprising:

acquiring a front image of the sample; and performing a second registration between the plurality of pieces of image data based on the front image prior to the first registration.

5. The OCT imaging method of claim 1, further comprising composing the plurality of pieces of image data to obtain composite image data, and extracting partial image data corresponding to the imaging region from the composite image data, wherein a series of processes of the extracting and composing the partial image data group, and a series of processes of the composing the plurality of pieces of image data and the extracting the partial image data, are selectively performed.

6. The OCT imaging method of claim 1, wherein the sample is an eye of a subject, and the information on the past imaging region and the information on the past target regions are stored in a medical data system.

7. The OCT imaging method of claim 6, further comprising accessing the medical data system with a communication device;

searching the medical system for past imaging region information and past target region information of the eye; and inputting searched past imaging region information and searched past target region information, wherein the designating the imaging region is performed using the searched past imaging region information, and the setting the plurality of target regions is performed using the searched past target region information.

* * * * *